US 11,779,551 B1

(12) United States Patent
Rein et al.

(10) Patent No.: US 11,779,551 B1
(45) Date of Patent: Oct. 10, 2023

(54) ANTITOXINS TO BREVETOXIN

(71) Applicants: Kathleen S. Rein, Miami, FL (US);
Yuan Liu, Miami, FL (US)

(72) Inventors: Kathleen S. Rein, Miami, FL (US);
Yuan Liu, Miami, FL (US)

(73) Assignee: THE FLORIDA INTERNATIONAL UNIVERISTY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 18/049,468

(22) Filed: Oct. 25, 2022

(51) Int. Cl.
*A61K 31/095* (2006.01)
*A61P 31/00* (2006.01)
*A61K 31/375* (2006.01)
*A61K 31/145* (2006.01)

(52) U.S. Cl.
CPC .......... *A61K 31/095* (2013.01); *A61K 31/145* (2013.01); *A61K 31/375* (2013.01); *A61P 31/00* (2018.01)

(58) Field of Classification Search
CPC .... A61K 31/335; A61K 31/35; A61K 31/365; A61K 31/366; A61P 43/00
See application file for complete search history.

(56) References Cited

PUBLICATIONS

Watkins et al. (Marine. Drugs 2008, 6, 431-455) (Year: 2008).*
Hendrickson, Robert G. et al. "What is the most appropriate dose of N-acetycysteine after massive acetaminophen overdose?" Clinical Toxicology 57(8):686-691, Feb. 19, 2019.
Jobson, Jordan et al. "Biomarkers of Brevetoxin Exposure in Human Lymphoblast Cells." Poster. Florida International University, Department of Chemistry and Biochemistry, (Year: 2022).
Mokhtari, Vida et al. "A Review on Various Uses of N-Acetyl Cysteine." Cell Journal 19(1):11-17, (Year: 2017).
Reddy, Vamsi & Winston, Nicole R. "Mesna." StatPearls [internet]. StatPearls Publishing, (Year: 2021).

* cited by examiner

*Primary Examiner* — Savitha M Rao
(74) *Attorney, Agent, or Firm* — SALIWANCHIK, LLOYD & EISENSCHENK

(57) ABSTRACT

The subject invention provides compounds as antitoxins for mitigating the toxic effects of algal toxins, e.g., brevetoxins. These compounds are mercaptan based compounds and derivatives that react rapidly with such toxins, e.g., brevetoxins and can be used to treat poisoning in a subject caused by such toxins. The subject invention also provides compositions comprising the mercaptan based compounds and derivatives for use to mitigate the toxic effects of brevetoxins. Further provided are methods of using the mercaptan based compounds and derivatives and compositions for treating and/or preventing brevetoxin poisoning in a subject such a human and marine animal.

13 Claims, 14 Drawing Sheets

Figure 4:
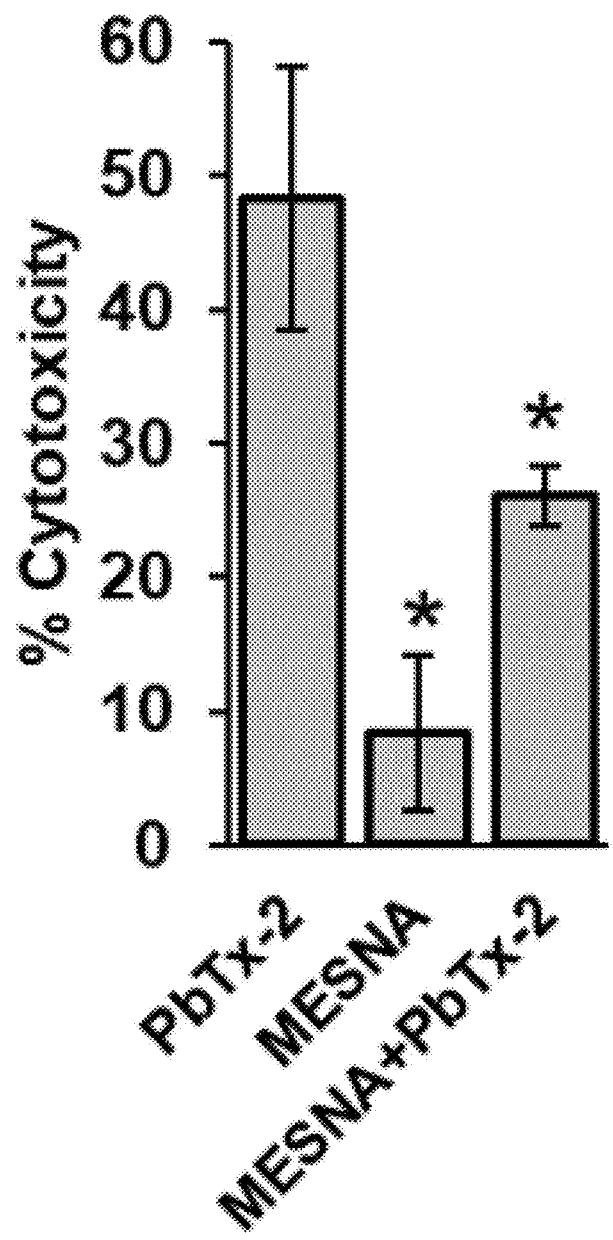

Specification includes a Sequence Listing.

PbTx-2 (brevetoxin B-type frame)

PbTx-1 (brevetoxin A-type frame)

FIG. 1

FIG. 2

PbTx-2 (5 µM) + AscA+ MESNA (100 µM each)
PbTx-2 (5 µM) + Cysteamine (100 µM)
PbTx-2 (5 µM) + Cystamine (disulfide) (50 µM)
PbTx-2 (5 µM) + MESNA 100 µM)
PbTx-2 (5 µM) + AscA (100 µM)
PbTx-2 (5 µM) alone % Cytotoxicity

FIG. 3

SEQUENCE LISTING

```
Sequence total quantity: 2
SEQ ID NO: 1              moltype =    length =
SEQUENCE: 1
000

SEQ ID NO: 2              moltype = AA   length = 27
FEATURE                   Location/Qualifiers
source                    1..27
                          mol_type = protein
                          organism = Homo sapiens
SEQUENCE: 2
CXXCXXXXXX XXXXXXXXXX XXXCXXC                                        27
```

ANTITOXINS TO BREVETOXIN

GOVERNMENT SUPPORT

This invention was made with government support under NA18NOS4780171 awarded by the National Oceanic and Atmospheric Administration. The government has certain rights in the invention.

SEQUENCE LISTING

The Sequence Listing for this application is labeled "SeqList-as-filed.xml," which was created on Oct. 25, 2022 and is 1,763 bytes. The Sequence Listing is incorporated herein by reference in its entirety.

BACKGROUND OF INVENTION

The dinoflagellate *Karenia brevis* is responsible for the Florida red tide, a type of harmful algal bloom (HAB) that occurs almost annually in the Gulf of Mexico. The consequences of this HAB include massive fish kills, marine mammal mortalities, closures of shellfish beds and fisheries, detrimental human health effects and significant losses to local economies that depend on fishing and tourism.

These negative outcomes have been attributed to the production of the neurotoxic brevetoxins by *K. brevis*. *K brevis* are lysed by wave action, particularly during blooms due the increase in the population density, causing the toxins to enter the water and then become aerosolized as sea spray. Aerosolized brevetoxins can be carried onshore by sea spray and produce respiratory distress among beachgoers and coastal residents. Aerosolized brevetoxins have been detected as far as over 6 kilometers inland during red tide events.

Humans are exposed to brevetoxins through food or aerosols and the effects vary depending on the route of exposure. Consumption of toxic shellfish can result in neurotoxic shellfish poisoning (NSP) with symptoms ranging from mild nausea to seizures, respiratory failure, and coma. Inhalation of aerosolized toxins may result in adverse respiratory effects such as bronchoconstriction and irritation of the eyes and throat. Respiratory symptoms have been shown to manifest more acutely among asthmatics. Florida red tide blooms have been associated with increases in emergency room admissions for digestive and respiratory complaints on the west coast of Florida.

Figure 1:
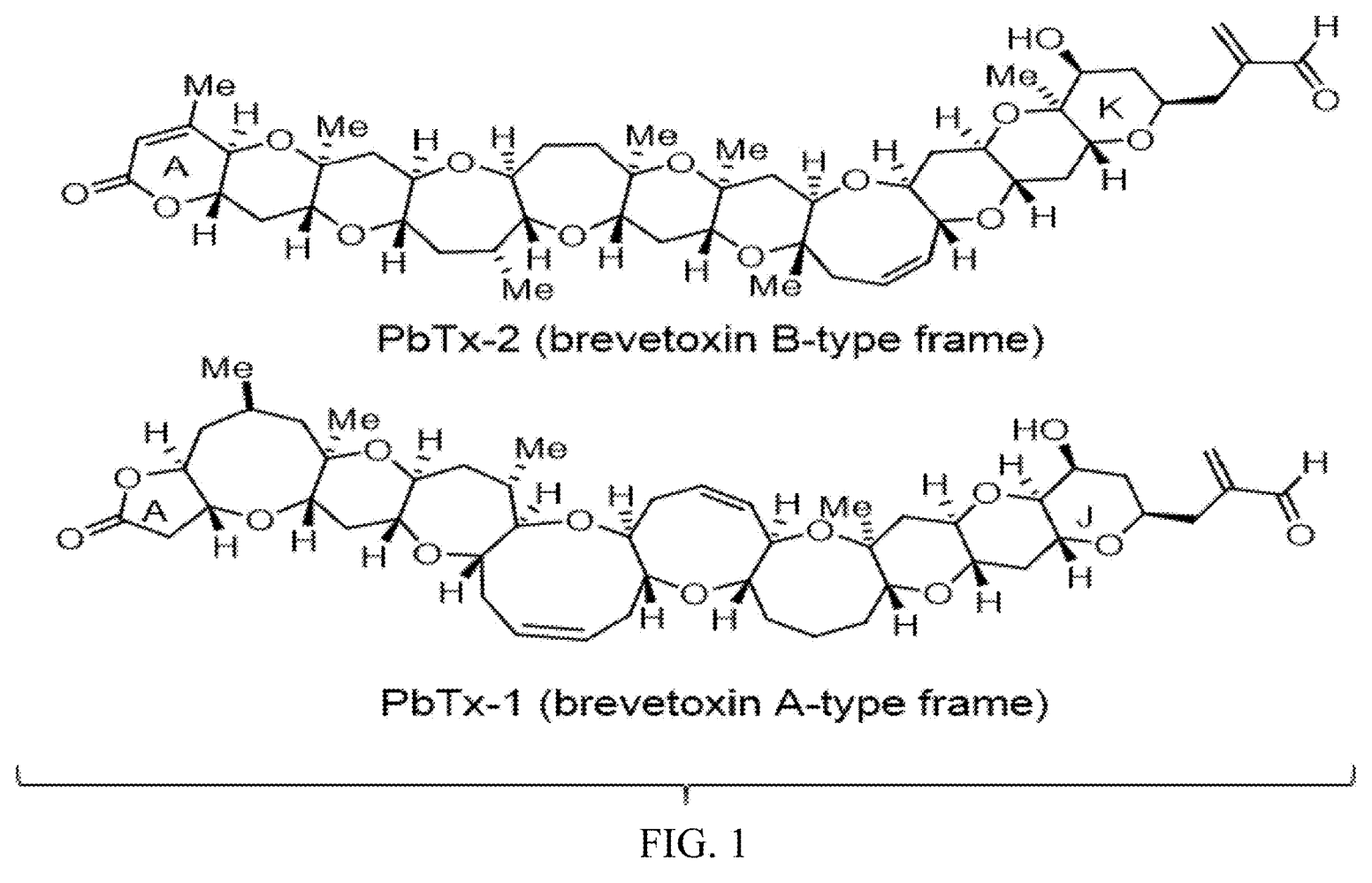

The brevetoxins are polyether ladder compounds with two distinct backbones (A and B) composed of a series of trans-fused ether rings with successive ether groups on alternating sides of the structure, a lactone A-ring and sidechain variants on the terminal ring (FIG. 1). PbTx-2, the most abundant of the brevetoxins has the B-type backbone and an α, β-unsaturated aldehyde sidechain. These neurotoxins bind to voltage-gated sodium channels (VGSCs) in excitable tissue, resulting in channel activation at normal resting potentials, depolarizing the cell and causing the neurological symptoms associated with NSP.

PbTx-2 is an inhibitor of mammalian thioredoxin reductase-1 (TrxR-1). TrxR along with its substrate thioredoxin (Trx), as the thioredoxin system, are presentin all living organisms and helps to maintain redox homeostasis within a cell. Trx regulates the activity of protein targets by reducing disulfide bridges by thiol disulfide exchange. During this process, Trx becomes oxidized and is returned to its reduced (active) state by the enzyme TrxR. TrxR transfers reducing equivalents from NADPH through a series of redox centers to its target Trx.

In mammals, TrxR is a homodimeric enzyme that contains the rare and highly reactive amino acid selenocysteine (Sec or U) in the penultimate position at the C-terminus (GCUG-COOH). Reduction of the homodimeric TrxR begins with the transfer of electrons from NADPH to FAD, followed by reduction of a disulfide bond at the N-terminus. Subsequently, a thiol disulfide exchange can proceed with the seleno-sulfide at the C-terminus. This renders the C-terminus poised for reduction of the oxidized thioredoxin. Reversible cysteine oxidation is an important post translational control mechanism that is regulated in part by this system.

The lower pKa for Sec compared to Cys in TrxR imparts higher activity to Sec-containing TrxR as it is more deprotonated under physiological conditions. This also makes Sec more susceptible to alkylation by electrophiles resulting in TrxR inhibition. Numerous compounds inhibit TrxR through this mechanism including α,β- unsaturated carbonyl compounds that react with the selenoate via a 1,4-conjugate addition reaction. Under these circumstances, TrxR can become a SecTRAP (Selenium Compromised Thioredoxin Reductase-derived Apoptotic Proteins). Rather than transferring reducing equivalents to Trx, electrons are transferred to molecular oxygen producing superoxide radical anion. In other words, TrxR becomes an NADPH oxidase. The enhanced ROS production coupled with the inhibition of disulfide bond reduction, leads to oxidative stress, and eventually to apoptosis.

With its α,β-unsaturated aldehyde sidechain, PbTx-2 has the requisite functionality to react with Sec through a 1,4-conjugate addition reaction. As a result of the inhibition of TrxR, cells are deprived of reduced Trx, redox-active thiols may become oxidized by excess ROS and the redox homeostasis of the proteome is disrupted, causing oxidative stress. Indicators of oxidative stress have been noted in marine life exposed to sub-lethal concentrations of brevetoxins in laboratory experiments or during red tide events. These include upregulation of thioredoxin, superoxide dismutase (SOD), NADH—ubiquinone oxidoreductase, glutathione-S-transferase as well as increased reactive oxygen and nitrogen species (ROS/RNS).

TrxR inhibition by PbTx-2 may be the link between red tide events and oxidative stress in marine life. The inhibition of TrxR inevitably leads to a shift in the redox status of cysteines within the proteome towards a more oxidized state. By differentially labelling free and reversibly oxidized cysteines, the shift in redox status of the proteome between two or more conditions may be quantified through redox proteomics analysis.

At this time, there is no treatment for brevetoxin poisoning. Thus, there is a need to identify and develop antitoxins to react with brevetoxins and interfere with the activity of brevetoxins on their biological targets.

BRIEF SUMMARY

The subject invention provides compounds, and salts thereof, as scavengers for toxins, such as brevetoxins, to mitigate their toxic effects. These compounds can be used as antitoxins for treating poisoning in a subject caused by, for example, algal toxins, e.g., brevetoxins. In one embodiment, the compounds are mercaptan based compounds, and derivatives thereof, that react rapidly with brevetoxins, e.g., brevetoxin congener PbTx-2, to mitigate their toxic effects.

Also, the mercaptan based drugs have antioxidant properties and can alleviate the oxidative stress induced by brevetoxins.

The subject invention also provides compositions comprising the compounds, and/or salts thereof, of the subject invention for use to mitigate the toxic effects of algal toxins such as brevetoxins. The composition further comprises a pharmaceutically acceptable carrier.

The subject invention further provides methods for treating or preventing poisoning in a subject caused by algal toxins, e.g., brevetoxins, the method comprising administering to the subject who has been poisoned by, exposed to, or at risk for exposure to, algal toxins, e.g., brevetoxins, the compound or salt thereof, or the composition comprising the compound or salt thereof of the subject invention.

The subject invention provides therapies for brevetoxin poisoning either through exposure by inhalation or consumption of contaminated shellfish.

In one embodiment, the subject invention provides a method for inhibiting or suppressing oxidative stress induced by algal toxins, e.g., brevetoxins, in a subject, the method comprising administering to the subject who has been poisoned by, exposed to, or at risk for exposure to, algal toxins, e.g., brevetoxins, the compound or salt thereof, or the composition comprising the compound or salt thereof of the subject invention.

In one embodiment, the subject invention provides a method for treating neurotoxic shellfish poisoning, the method comprising administering to the subject who has consumed brevetoxin tainted shellfish the compound or salt thereof, or the composition comprising the compound or salt thereof of the subject invention.

BRIEF DESCRIPTION OF DRAWINGS

FIG. 1 shows the structures of brevetoxins.

FIG. 2 shows adducts formed between PbTx-2 and mercaptans.

FIG. 3 shows the co-administration of MESNA, ascorbic acid or cysteamine (100 μM) along with PbTx-2 (5 μM) to lymphoblast cells for 24 hr measured by LDH activity. AscA=ascorbic acid. Test compounds showed no cytotoxicity up to the highest concentration tested (500 μM).

FIG. 4 shows the cytotoxicity (by LDH assay) of PbTx-2 (5 μM), MESNA (100 μM) and PbTx-2 (5 μM) & MESNA (100 μM) relative to untreated human lymphoblast cells.

FIG. 5 shows a schematic representation of Redox Proteomics using both "light" and "heavy" tandem mass tags (TMTs) to differentially label proteins. The location of the labels for TMT126 (star) and TMT131 (circle) are shown in the diagram.

FIGS. 6A-6D show histograms of redox states for all 2617 individual proteins isolated from lymphoblast cells A) Control. B) PbTx-2 (5 μM) C) PbTx-2 (5 μM) & MESNA (500 μM) and D) Box and whisker plot of redox states for the 606 proteins that appeared in three or more replicate treatments. Left: control; middle: PbTx-2 (5 μM) & MESNA (500 μM); right: PbTx-2 (5 μM).

FIGS. 7A-7B show volcano plots of loge of fold change in redox state vs $\log_{10}$p for the 606 individual proteins that occurred in 3 or more replicates for A) PbTx-2 (5 μM) vs. Control. B) PbTx-2 (5 μM) & MESNA (500 μM) vs Control.

FIGS. 8A-8C show bar graphs for pathways with significantly altered redox status. A) Bar graph of $-\log_{10}$p for proteins significantly altered in redox status (p<0.05) relative to control in the PbTx-2 treated samples sorted into major metabolic pathways according to KEGG ontology for PbTx-2 (5 μM) treatment (solid bars) and the same proteins in the PbTx-2 (5 μM) & MESNA (500 μM) treatment (striped bars). The two major pathways B) genetic information processing and C) metabolism further subdivided.

FIGS. 9A-9B show volcano plots of loge of fold change in expression vs $\log_{10}$ p for the 606 individual peptides which occurred in 3 or more replicates for A) PbTx-2 (5 μM) vs. Control; B) PbTx-2 (5 μM) & MESNA (500 μM) vs Control.

FIG. 10 shows volcano plots of loge of fold change in expression vs $\log_{10}$ p for the 14 proteins that were significantly different from the control in both the PbTx-2 (5 μM, ■) and the PbTx-2 (5 μM) and MESNA (500 μM, ●) treated cells.

FIGS. 11A-11C show bar graphs for proteins with altered expression. A) Bar graph of −25 $\log_{10}$ p for proteins significantly altered in expression (p<0.05) relative to control in the PbTx-2 treated samples sorted into major metabolic pathways according to KEGG ontology for PbTx-2 (5 μM) treatment (solid bars) and the same proteins in the PbTx-2 (5 μM) & MESNA (500 μM) treatment (striped bars). The two major pathways B) genetic information processing and C) metabolism further subdivided. In B) and C), proteins in transcription/translation, ribosomal proteins, membrane trafficking, replication & repair, protein phosphatases &associated proteins, nucleotide metabolism, and carbohydrate metabolism subdivisions are downregulated while proteins in folding/sorting degradation and peptidases & inhibitors subdivisions are upregulated.

FIGS. 12A-12B show percentage of proteins that were identified in three or more biological replicates localized by A) the Human Protein Atlas or B) Deeploc 2.0. The fraction of proteins by location that were unchanged, significantly altered (p≤0.05) in redox state, and significantly altered in expression in the PbTx-2 treated samples relative to control are shown in black, gray and light gray, respectively. In panel A, the 250 proteins localized to the nucleus includes Nuclear Speckles, Nuceloplasm, Nucleoli, Nuclear Membrane, Centriolar Satellites, Centrosome.

BRIEF DESCRIPTION OF SEQUENCES

SEQ ID NO: 1 is a N-terminal sequence motif of peroxyredoxins contemplated for use according to the subject invention.

SEQ ID NO: 2 is the sequence of a $H_2O_2$-sensitive $Zn^{2+-}$finger motif of eIF2β contemplated for use according to the subject invention.

DETAILED DISCLOSURE

The subject invention provides compounds, and salts thereof, as scavengers for toxins such as brevetoxins, to mitigate their toxic effects. These compounds can be used as antitoxins for treating poisoning in a subject caused by algal toxins, e.g., brevetoxins. In a preferred embodiment, the toxins comprise an alpha beta unsaturated carbonyl.

In one embodiment, the compounds are mercaptan based compounds, and derivatives thereof, that react rapidly with brevetoxins, e.g., brevetoxin congener PbTx-2, to mitigate their toxicities. Also, the mercaptan based drugs have antioxidant properties and can alleviate the oxidative stress induced by brevetoxins.

In one embodiment, the mercaptan based compounds and derivatives have a general structure of $$\text{HS} \diagdown \underset{R_1}{\overset{R_2}{\diagup}}$$

wherein $R_1$ and $R_2$ are each independently selected from, for example, hydrogen, $NR_3R_4$, alkyl, substituted alkyl, aryl, substituted aryl, alkoxyl, carboxyl, sulfonyl, sulfo, acyl, vinyl, propargyl, ether, thioether, nitrile, amido, thiocyano, carbamoyl, imino, and nitro, wherein $R_3$ and $R_4$ are each independently selected from, for example, acyl, hydrogen, alkyl, substituted alkyl, carbonyl, and ketone.

In one embodiment, the mercaptan based compounds and derivatives have a general structure of $$\text{HS} \diagdown \underset{\underset{H}{N} \diagdown R_3}{\overset{R_2}{\diagup}},$$

wherein $R_2$ is selected from, for example, hydrogen, NR3R4, alkyl, substituted alkyl, aryl, substituted aryl, alkoxyl, carboxyl, sulfonyl, sulfo, and acyl, and each $R_3$ is selected from, for example, hydrogen, alkyl, substituted alkyl, carbonyl, acyl and ketone.

In a specific embodiment, $R_1$ is hydrogen and $R_2$ is —$SO_3Na$, $NH_2$, or $NHCOCH_3$.

In a specific embodiment, $R_1$ is $NHR_3$, $R_2$ is carboxyl, and $R_3$ is hydrogen or $COCH_3$.

In a specific embodiment, the mercaptan based compounds are sodium mercaptoethyl sulfonate (MESNA)

$$\text{HS} \diagdown \underset{\underset{\overset{\ominus}{O} \; \overset{\oplus}{Na}}{\overset{\|}{S}}}{\overset{O}{\|}} O,$$

cysteamine, N-acetyl cysteamine or N-acetyl cysteine.

In a specific embodiment, when $R_1$ is —COOH, and $R_2$ is $NR_3R_4$, $R_3$ and $R_4$ cannot be H at the same time.

The subject invention also provides compositions comprising the compound, or salt thereof, of the subject invention for use to mitigate the toxic effects of algal toxins such as brevetoxins. In one embodiment, the pharmaceutical composition of the subject invention comprises the compound of the subject invention or a salt thereof. The composition further comprises a pharmaceutically acceptable carrier.

In one embodiment, the composition of the subject invention further comprises ascorbic acid, which, in combination with the mercaptan based compounds or derivatives, provides a synergistic effect on mitigating the toxicity of brevetoxins.

The mercaptan based compounds and derivatives, according to embodiments of the invention, can be provided separately or in combination with medicaments that are, for example, antibacterial, antiviral, antifungal, or any combination thereof. The medicaments can be formulated according to known methods for preparing pharmaceutically useful compositions. Such pharmaceutical compositions can be adapted for various forms of administration, such as, but not limited to, oral, parenteral, nasal, topical, and transdermal.

The mercaptan based compounds and derivatives can be provided as solutions, amorphous compounds, injectables, pills, inhalants, or in any other form for administration. Formulations are described in a number of sources, which are well known and readily available to those skilled in the art.

Formulations suitable for administration include, for example, aqueous sterile injection solutions, which can contain antioxidants, buffers, bacteriostats, and solutes, which render the formulation isotonic with the blood of the intended recipient; and aqueous and non-aqueous sterile suspensions that can include suspending agents and thickening agents. The formulations can be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, or tablets of the compositions. It should be understood that in addition to the ingredients particularly mentioned above, the formulations of the subject invention can include other agents conventional in the art having regard to the type of formulation in question.

Pharmaceutically acceptable carriers used in formulations include, but are not limited to, inert diluents and vehicles such as: one or more excipients, buccal tablets, troches, capsules, elixirs, suspensions, syrups, wafers, and aerosol sprays. Tablets, troches, pills, capsules, and the like may, but do not necessarily, contain binders, such as gum tragacanth, acacia, corn starch or gelatin; excipients, such as dicalcium phosphate; a disintegrating agent, such as corn starch, potato starch, or alginic acid; a lubricant, such as magnesium stearate; a sweetening agent, such as sucrose, fructose, lactose or aspartame; flavoring agent, such as peppermint, oil of wintergreen, or cherry flavoring; a liquid carrier, such as a vegetable oil or a polyethylene glycol; and/or solid carriers; such as finely divided solids such as talc, clay, microcrystalline cellulose, silica, or alumina. Any material used in preparing the dosage form should be pharmaceutically acceptable and substantially non-toxic in the amounts employed. The dosage form may be a sustained-release preparation. Other dosage forms can include surfactants or other adjuvants.

Particularly, the carrier and/or diluent should not deteriorate the pharmacological potency of the active agent and the capability of the complex to be directed to a desired target within, or on, the animal body. Preferably, said carrier and/or diluent is/are selected from water, physiologically acceptable aqueous solutions containing salts and/or buffers and any other solution acceptable for administration to an animal. Such carriers and diluents are well known to a person skilled in this field and can be, for example, distilled water, de-ionized water, pure or ultrapure water, saline, phosphate-buffered saline (PBS), solutions containing usual buffers which are compatible with the other components of the drug targeting system etc.

In some embodiment, compounds as described herein may be in the form of a pharmaceutically acceptable salt. Pharmaceutically acceptable salt as used herein includes, for example, salts that have the desired pharmacological activity of the parent compound (salts which retain the biological effectiveness and/or properties of the parent compound and which are not biologically and/or otherwise undesirable). The salt may be, for example, a sodium, potassium, calcium, or magnesium salt. The acid salts can be generated with any pharmaceutically acceptable organic or inorganic acid.

Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Salts, as described herein, may be prepared by conventional processes known to a person skilled in the art, for example, and without limitation, by combining the free form with an organic acid or cation exchange from other salts. Those skilled in the art will appreciate that preparation of salts may occur in situ during isolation and purification of the compounds or preparation of salts may occur by separately reacting an isolated and purified compound.

In some embodiments, the compounds may be in the form of a solvate. Solvates contain either stoichiometric or nonstoichiometric amounts of a solvent in physical association the compound or salt thereof. The solvent may be, for example, and without limitation, a pharmaceutically acceptable solvent. For example, hydrates are formed when the solvent is water or alcoholates are formed when the solvent is an alcohol.

In certain embodiments, the composition is in a powder form. The pharmaceutically accepted carrier is a finely divided solid that is in a mixture with the finely divided active compounds. In another embodiment, the composition is in a tablet form. The active component is mixed with the pharmaceutically accepted carrier having the necessary binding capacity in suitable proportions and compacted in desired shape and size. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

In specific embodiments, the dry powder composition according to the invention may be filled into the reservoir of a single dose or multidose dry powder inhaler.

In one embodiment, the composition can be applied directly to the nasal cavity by conventional means, for example with a dropper, pipette or spray. The compositions may be provided in single or multi-dose form. Administration to the respiratory tract may also be achieved by means of an aerosol formulation in which the active ingredient is provided in a pressurized pack with a suitable propellant such as a chlorofluorocarbon (CFC) for example dichlorodifluoromethane, trichlorofluoromethane, or dichlorotetrafluoroethane, carbon dioxide, or other suitable gas.

The effective amount of said pharmaceutical composition can be administered through, for example, oral, rectal, bronchial, nasal, topical, buccal, sub-lingual, transdermal, vaginal, intramuscular, intraperitoneal, intravenous, intraarterial, intracerebral, interaocular administration or in a form suitable for administration by inhalation or insufflation, including powders and liquid aerosol administration, or by sustained release systems such as semipermeable matrices of solid hydrophobic polymers containing the compound(s) of the invention. Administration may be also by way of other carriers or vehicles such as patches, micelles, liposomes, vesicles, implants (e.g., microimplants), synthetic polymers, microspheres, nanoparticles, and the like.

In one embodiment, the composition is formulated for parenteral administration (e.g., by injection, for example bolus injection or continuous infusion). In addition, the composition may be presented in unit dose form in ampoules, pre-filled syringes, and small volume infusion or in multi-dose containers with or without an added preservative. The compositions may be in forms of suspensions, solutions, or emulsions in oily or aqueous vehicles. The composition may further contain formulation agents such as suspending, stabilizing and/or dispersing agents.

In certain embodiments, the composition is applied topically or systemically or via a combination of both. The composition may be formulated in the forms of lotion, cream, gel and the like.

The mercaptan based compounds and derivatives or pharmaceutical compositions for use as described herein may be administered by means of a medical device or appliance such as an implant, graft, prosthesis, stent, etc. Also, implants may be devised which are intended to contain and release such compounds or compositions. An example would be an implant made of a polymeric material adapted as a vehicle to release the mercaptan based compounds and derivatives over a period of time.

The subject invention further provides methods for treating or preventing poisoning in a subject caused by algal toxins, e.g., brevetoxins. In one embodiment, the method for treating brevetoxin poisoning in a subject comprises administering to the subject who has been poisoned by, exposed to, or at risk for exposure to, the brevetoxin the compound/antitoxin, or salt thereof, or the composition comprising the compound/antitoxin, or salt thereof of the subject invention.

In one embodiment, the subject invention provides a method for reducing brevetoxin toxicity in a subject, the method comprising administering to the subject who has been poisoned by, exposed to, or at risk for exposure to, the brevetoxin the compound/antitoxin, or salt thereof, or the composition comprising the compound/antitoxin, or salt thereof of the subject invention.

In one embodiment, the subject invention provides a method for reducing brevetoxin toxicity in a cell, the method comprising contacting/exposing/treating the cell that has been exposed to the brevetoxin the compound/antitoxin, or salt thereof, or the composition comprising the compound/antitoxin, or salt thereof of the subject invention.

In one embodiment, the subject invention provides a method for inhibiting or suppressing oxidative stress induced by a brevetoxins in a subject, the method comprising administering to the subject who has been poisoned by, exposed to, or at risk for exposure to, the brevetoxin the compound/antitoxin, or salt thereof, or the composition comprising the compound/antitoxin or salt thereof of the subject invention.

In one embodiment, the subject invention provides a method for inhibiting or suppressing oxidative stress induced by a brevetoxin in a cell, the method comprising contacting/exposing/treating the cell that has been exposed to the brevetoxin the compound/antitoxin, or salt thereof, or the composition comprising the compound/antitoxin or salt thereof of the subject invention.

In one embodiment, the subject invention provides a method for scavenging or reducing the level of a toxic metabolite of a chemotherapy drug in a subject, the method comprising administering the compound/antitoxin, or salt thereof, or the composition comprising the compound/antitoxin, or salt thereof, of the subject invention to the subject who has been administered with the cancer drug.

In a specific embodiment, the chemotherapy drug is isophosphamide or cyclophosphamide. In a preferred embodiment, the toxic metabolite of the cancer drug comprises an α, β-unsaturated aldehyde. In a specific embodiment, the toxic metabolite is, for example, acrolein.

In one embodiment, the subject invention provides a method for inhibiting or blocking the interaction of brevetoxins with TrxR in a cell, the method comprising contacting the cell with the compound/antitoxin, or salt thereof or the composition comprising the compound/antitoxin or salt thereof of the subject invention In one embodiment, the subject invention provides a method for treating neurotoxic shellfish poisoning, the method comprising administering to the subject who has consumed brevetoxin tainted shellfish the compound/antitoxin, or salt thereof, or the composition comprising the compound/antitoxin, or salt thereof of the subject invention.

In one embodiment, the subject invention provides a method for treating a respiratory distress induced by an algal toxin, e.g., brevetoxin, in a subject, the method comprising administering to the subject who has been poisoned by, exposed to, or at risk for exposure to, the algal toxin, e.g., brevetoxin, the compound or salt thereof, or the composition comprising the compound or salt thereof of the subject invention.

In one embodiment, the method of the subject invention further comprises detecting/measuring the level of algal toxin, e.g., brevetoxin, in a sample of the subject prior to or after the administration of the compound or the composition of the subject invention.

An "effective amount" of a pharmaceutical composition includes a therapeutically effective amount or a prophylactically effective amount. A "therapeutically effective amount" refers to an amount effective, at dosages and for periods of time necessary, to achieve the desired therapeutic result. A therapeutically effective amount of a formulation may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result. Typically, a prophylactic dose is used in subjects prior to a condition or disease, so that a prophylactically effective amount may be less than a therapeutically effective amount.

Dosage values may vary with the severity of the condition to be alleviated. For any particular subject, specific dosage regimens may be adjusted over time according to the individual need and the professional judgment of the person administering or supervising the administration of the compositions. Dosage ranges suggested herein are exemplary only and do not limit the dosage ranges that may be selected by medical practitioners. The amount of the mercaptan based compounds and derivatives in the composition may vary according to factors such as the disease state, age, sex, and weight of the subject. Dosage regimens may be adjusted to provide the optimum therapeutic response.

In general, the mercaptan based compounds and derivatives should be used without causing substantial toxicity. Toxicity of the mercaptan based compounds and derivatives can be determined using standard techniques, for example, by testing in cell cultures or experimental animals and determining the therapeutic index. In some circumstances, however, such as in severe disease conditions, it may be appropriate to administer substantial excesses of the compositions.

The term "subject" or "patient," as used herein, describes an organism, including mammals such as primates. Mammalian species that can benefit from the disclosed methods of treatment include, but are not limited to, apes, chimpanzees, orangutans, humans, and monkeys; domesticated animals such as dogs, cats; live stocks such as horses, cattle, pigs, sheep, goats, and chickens; and other animals such as mice, rats, guinea pigs, and hamsters. In specific embodiments, the subject is a human or marine animal.

The terms "treatment" or any grammatical variation thereof (e.g., treat, treating, etc.), as used herein, includes but is not limited to, the application or administration to a subject (or application or administration to a cell or tissue from a subject) with the purpose of slowing, stabilizing, curing, healing, alleviating, relieving, remedying, less worsening, ameliorating, or improving the disease or condition. The term "treating" refers to any indication of success in the treatment or amelioration of a pathology or condition, including any objective or subjective parameter such as abatement; remission; lessening of the rate of worsening; lessening severity of the disease; stabilization, diminishing of symptoms or making the pathology or condition more tolerable to the subject; or improving a subject's physical or mental well-being.

The compositions can be administered to a subject by methods including, but not limited to, (i) administration through oral pathways, which administration includes administration in capsule, tablet, granule, spray, syrup, or other such forms; (ii) administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, or the like; as well as (iii) administration topically, or as deemed appropriate by those of skill in the art for bringing the compound into contact with living tissue; and (iv) administration via controlled released formulations, depot formulations, and infusion pump delivery.

Furthermore, it would be understood by those skilled in the art that the methods described in the present invention would not only apply to treatment in a subject, but could be applied to cell cultures, organs, tissues, or individual cells in vivo or in vitro, including immortalized cells isolated or derived from a subject.

The present invention also provides kits comprising the compounds and/or pharmaceutical compositions as described herein. The kits may further be used in the methods described herein. The kits may also include at least one reagent and/or instruction for their use. Moreover, the kits may include one or more containers filled with one or more compounds and/or pharmaceutical composition described in the present invention.

As used herein, the singular forms "a," "an," and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof), such as "comprising," "comprises," and "comprise," can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of concentrations of ingredients where the term "about" is used, these values include a variation (error range) of 0-10% around the value (X±10%).

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

EXAMPLES

Materials and Methods

General Experimental Details.

The iodoTMT sixplex reagent set, trypsin protease (MS grade), immobilized anti-TMT resin, and TMT elution buffer) and all other reagents were purchased from Fisher Scientific unless otherwise specified. Absorbance measurements were made on a Synergy 2 multi-detection microplate reader. Brevetoxin (PbTx-2) was purified from laboratory cultures of *K brevis*. Human lymphoblast cells (GM05581) were purchased from the Coriell Institute for Medical Research. Lactate dehydrogenase assay kit was purchased from Cayman Chemical and used according to the manufacturer's instructions.

Growth and Treatment of Cells

Human lymphoblast cells were cultured in Roswell Park Memorial Institute (RPMI) 1640 medium. The RPMI 1640 was supplemented with 15% fetal bovine serum and the cells were grown at 37° C. in a humidified incubator. Once the cells had grown to at least $2.0 \times 10^7$, they were treated with either 5 μM PbTx-2 (by a 1:800 dilution of a 4 mM stock solution) or 500 μM MESNA and 5 μM PbTx-2 or a volume of DMSO (vehicle) equivalent to that used for treated samples as control, for 24 hours. Cells were centrifuged at 720 X g for 4 min, the medium was removed and reserved for lactate dehydrogenase (LDH) assay. The cell pellet was resuspended in growth medium and centrifuged at 720 x g for 4 minutes. The supernatant was removed, and the cell pellets were then ready for lysis to begin the protein isolation process. Cells were lysed through four freeze and thaw cycles, using liquid nitrogen to freeze the cells. Five replicates of each treatment were prepared.

Protein isolation and quantitation

Lysed cells were resuspended in a 1 mL solution of saturated trichloroacetic acid (0.2 mL) and acetone (0.8 mL) for 12-16 hours at −20° C. to precipitate the proteins. The precipitated protein suspension was centrifuged at 17000 x g, 4° C., for 30 minutes, and the supernatant was discarded. Pellets were washed in 80% acetone and 20% deionized $H_2O$, followed by two washes with 100% acetone. The suspensions were centrifuged at 17000 x g, 4° C., for 20 minutes after each wash.

Pellets were air-dried at 50° C. for 5 minutes and suspended in no more than 50μL of warm 6 M guanidine-HCl and incubated at 50° C. for no more than 10 minutes periodically aspirating the suspension with a pipette to facilitate solubilization of the proteins. An equal volume (up to 504) of HES buffer at 50° C. (50 mM HEPES, EDTA 1 mM, SDS 0.1% pH 8) was added, and the suspensions were centrifuged at 17,000 x g, at ambient temperature for 5 min. Additional guanidine-HCl can be added to dissolve the pelleted proteins if necessary. A second 6 M guanidine-HCl and HES buffer incubation of the residual pellet may be performed to increase the yield in the event that the initial yield of protein is insufficient to complete the experiment. The supernatants were pooled and the pellets containing cellular debris and precipitated SDS were discarded. Five (5) μL of the protein extracts were diluted 10-20-fold in HES/2 buffer, for quantitation of protein content by Bradford assay against a standard curve of BSA (1 mg/mL to 0.0325 mg/mL) in HES/2 buffer. Ten (10) μL of each standard or sample was combined with 90 of Pierce 660 nm Protein Assay Reagent in triplicate in a 384 well plate. Absorbance was measured at 660 mn immediately and again after 5 minutes. Protein extracts were diluted with HES/2 buffer to 1.25 mg/mL, per instructions of the manufacturer.

Thiol Quantitation

When sufficient volume was available (a minimum of 125 μL) after dilution of the protein extracts to 1.25 mg/mL, 25 μL was used to determine thiol concentrations by reaction with DTNB (5,5'—Dithio-Bis (2-Nitrobenzoic Acid)) against a standard curve of cysteine (0-1 mM) in phosphate buffer (100 mM $Na_2HPO_4$, 1 mM EDTA, pH 8.0). Eighty (80) μL of the standards/samples were combined with 20 μL of DTNB (10 mM in phosphate buffer), in triplicate. Samples were diluted 1:10 or 1:20 with HES/2 buffer as needed.

First Labelling

Both labelling reactions were carried out in the dark for one hour at 37° C. Ten (10) μL of iodoTMT reagent (20

µg/µL in LCMS grade methanol) were added to 100 µL of protein extract at a concentration of 1.25 mg/ml in HES/2 buffer. For the first labels, iodoTMT-126 was used for the control treatments, iodoTMT-127 was used for the combination of 500 µM MESNA and 5 µM PbTx-2 treatments, and iodoTMT-128 was used for the 5 µM PbTx-2 treatments. Excess iodoTMT label was removed by adding 660 µL of acetone chilled at −20° C., followed by overnight precipitation at −20° C. The precipitated protein suspensions were centrifuged at 17,000 x g, 4° C., for 30 minutes and the supernatants discarded.

Second Labelling

The precipitated proteins from the first labeling reaction were dissolved in 100 µL of HES/2 buffer. One (1) µL of 0.5 M TCEP (Tris(2-carboxyethyl) phosphine) was added to each pellet, and the reaction incubated at 50° C. for one hour. To the reduced protein solution 10 µL of iodoTMT label (20 µg/µL in LCMS grade methanol) was added, and the reaction mixtures were incubated under the conditions described above for the first labelling reaction. For the second labels, iodoTMT-129 was used for the control treatments, iodoTMT-130 was used for the combination of 500 µM MESNA and 5 µM PbTx-2 treatments, and iodoTMT-131 was used for the 5 µM PbTx-2 treatments. To quench unreacted iodoTMT label, a solution of DTT (dithiothreitol) in deionized water was prepared and added to the labeling reactions such that the final concentration of DTT 20 mM. The reactions were incubated at 37° C., for 20 minutes. Labeled proteins from the three treatments (control, 500 µM MESNA and 5 µM PbTx-2, and 5 µM PbTx-2) were combined, and precipitated by adding 6 times the combined sample volume of chilled acetone followed by overnight precipitation at −20° C.

Trypsin Digestion, Enrichment, and Elution

The protein suspensions were centrifuged for 30 minutes at 17,000 x g at 4° C., and the supernatant discarded. The protein pellets were washed with 1 mL of acetone and centrifuged again at 17,000 x g at 4° C. The supernatant was discarded, and the pellets were resuspended in warm 50 mM Tris buffer, 1 mM EDTA at pH 8 and incubated at 37° C. for one hour. Trypsin digestion was initiated by the addition of 7 µg of trypsin (7 µL of a 1 mg/mL solution in 50 mM acetic acid) for every 250 µg of protein followed by overnight incubation at 37° C.

The trypsinization reaction was halted by the addition of 1 µL of trifluoroacetic acid (TFA). The solution was lyophilized in a centrifugal evaporator after freezing it at =80° C. The lyophilized peptide mixture was taken up in 100 µL Tris-Buffered-Saline (TBS, 10 mM Tris, 100 mM NaCl) and incubated with anti-TMT resin end-over-end rocking overnight at 4° C. The binding capacity of the resin for the TMT mass reporter is ≈25 nmol/mL of resin and 750 µL of settled resin was used, which is twice the minimum recommended amount per 100 µg of protein. The peptides were eluted from the resin according to the manufacturer's instructions, lyophilized, frozen at −80° C., and shipped on dry ice for proteomic analysis.

Proteomic Analysis

Samples were analyzed at the UTSW Proteomics Core by LC-MS/MS analysis. Samples underwent solid-phase extraction cleanup with an Oasis HLB plate (Waters) and injected onto an Orbitrap Fusion Lumos mass spectrometer coupled to an Ultimate 3000 RSLC-Nano liquid chromatography system. Labeled peptides were separated on a 75 um i.d., 75-cm long EasySpray column (Thermo) using a gradient from 0-28% buffer B over 180 min. Buffer A contained 2% (v/v) ACN and 0.1% formic acid in water, and buffer B contained 80% (v/v) ACN, 10% (v/v) trifluoroethanol, and 0.1% formic acid in water at a flow rate of 250 nL/min. The mass spectrometer operated in positive ion mode with a source voltage of 1.8 kV and an ion transfer tube temperature of 275° C. MS scans were acquired at 120,000 resolution in the Orbitrap and top speed mode was used for SPS-MS3 analysis with a cycle time of 2.5 s. MS2 was performed with collisionally-induced dissociation with a collision energy of 35%. The top 10 fragments were selected for MS3 fragmentation using HCD, with a collision energy of 58%. Dynamic exclusion was set for 25 s after an ion was selected for fragmentation.

Raw MS data files were analyzed using Proteome Discoverer v2.4 (Thermo), with peptide identification performed using Sequest HT searching against the human protein database from UniProt (downloaded Sep. 20, 2021, 78120 entries). Fragment and precursor tolerances of 10 ppm and 0.6 Da were specified, and three missed cleavages were allowed. Oxidation of Met and iodoTMT6plex addition on Cys were set as variable modifications. The false-discovery rate (FDR) cutoff was 1.

Treatment of Data

The gene symbols of the reported proteins were used to retrieve their KEGG (Kyoto Encyclopedia of Genes and Genomes) Orthology (KO) classification. KO identifiers were used to group proteins according to general primary and secondary functions. Gene codes were entered into the Human Protein Atlas (www.proteinatlas.org) for subcellular localization of identified proteins. Accession numbers were used to obtain full-length amino acid sequences via BLASTp search on the National Center for Biotechnology Information (NCBI) protein database, and the full-length sequences obtained were used to predict subcellular locations via DeepLoc 2.0 predictions online.

Reporter intensities were used to calculate redox states for individual peptides. The redox state of a peptide, or the fraction of cysteines in the reduced state, is the ratio of intensities of the light TMT reporter to the sum of intensities of the light plus heavy TMT reporter for each individual peptide.

$$\text{Redox State}(x) = \frac{TMT_x^{light}}{TMT_x^{light} + TMT_x^{heavy}} \quad (1)$$

Reporter intensities for individual peptides were summed ($TMTx^{light}$ plus $TMTx^{heav}$) and normalized to total reporter intensity within each treatment for expression analysis and calculation of fold change.

EXAMPLE 1-MERCAPTAN BASED COMPOUNDS AS ANTITOXINS OF BREVETOXINS

Mercaptan based compounds were tested for their effectiveness as antitoxins to the most abundant of the brevetoxins, PbTx-2, which comprises 80-85% of the toxin profile. Four mercaptan based compounds that were tested are MESNA, cysteamine, N-acetyl cysteamine, and N-acetyl cysteine, which exhibit low toxicities.

Figure 2:
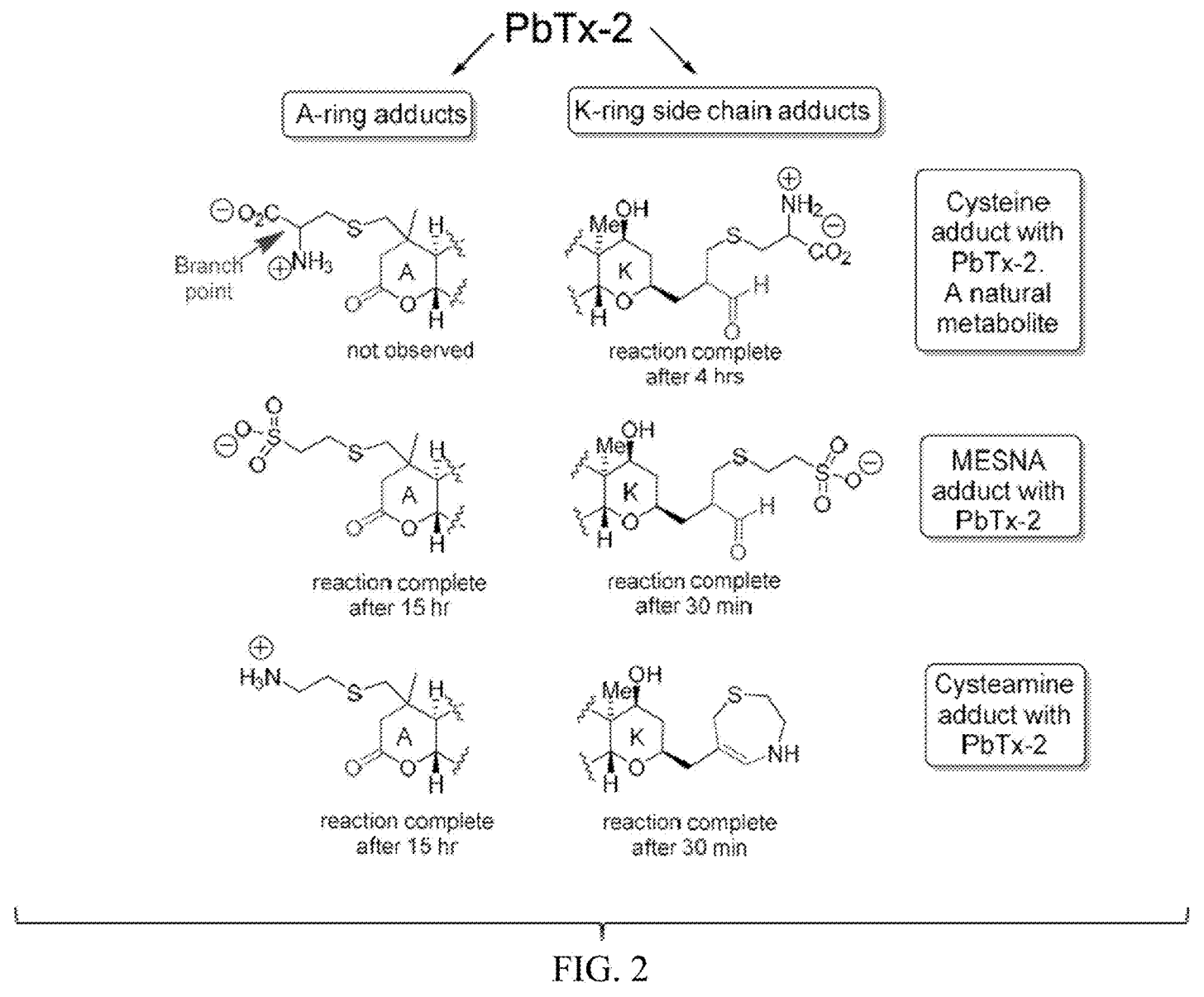

PbTx-2 possesses two α, β-unsaturated carbonyl groups (FIG. 1). Both groups are susceptible to attack by mercaptans. Indeed, a common metabolite of PbTx-2 is the adduct with cysteine at the K-ring side chain shown in FIG. 2. Mass spectrometric analysis of reaction mixtures has shown that MESNA and cysteamine react rapidly and quantitatively with the PbTx-2 side chain within 15 minutes of mixing under mild conditions (room temperature).

Furthermore, MESNA and cysteamine also react with the A-ring lactone quantitatively after 15 hours. On the other hand, the reaction with cysteine was complete only after four hours, and the A-ring adduct with cysteine was not observed, nor has it been reported in the literature. Similarly, the reaction between PbTx-2 and glutathione (GSH) is very sluggish (days) even in the presence of glutathione-S-transferase. The lower reactivity of cysteine and GSH compared to MESNA and cysteamine is likely due to steric effects that arise from the branching of cysteine and GSH only one carbon removed from the reactive thiol groups.

Reliance on natural detoxification pathways is ineffective. Neither cysteine nor GSH react rapidly with PbTx-2. Cysteine reacts much faster than GSH, but the concentration of free cysteine within a cell is relatively low (250-400 µM). While cysteine conjugation enhances excretion by increasing water solubility, this metabolite still binds at the principal target of brevetoxins, the voltage-gated sodium channel (VGSC). Because alterations of the A-ring lactone reduce or eliminate VGSC affinity, rapidly reacting antitoxins, in particular those that act on the A-ring lactone, could be used as treatments or prophylactics against the adverse effects of brevetoxicosis in humans and marine animals in cases of exposure via inhalation or ingestion.

Co-administration of PbTx-2 (5 µM) along with MESNA or cysteamine (100 µM) significantly reduced cytotoxicity of PbTx-2 to human lymphoblast cells (as measured by LDH activity) after 24 hr exposure. FIG. 3 shows the results of these experiments. All treatments reduced the cytotoxicity of PbTx-2, and these differences were statistically significant. It is noteworthy that cysteamine and the corresponding disulfide cysteamine were equally effective, implying in vivo reduction of the disulfide bridge.

Because PbTx-2 has been shown to induce oxidative stress, the effectiveness of the antioxidant ascorbic acid was tested. Co-administration of ascorbic acid and MESNA reduced cytotoxicity to nearly control levels (the difference from the control was not statistically significant, p=0.10, n=5). Mercaptans have antioxidant properties; however, ascorbic acid and MESNA act by different mechanisms given the apparent synergistic effect of co-administration.

EXAMPLE 2-CHANGES IN REDOX STATUS

Cytotoxicity assays were performed on human lymphoblast cells treated with PbTx-2 (5 µM), PbTx-2 (5 µM) & the acrolein scavenger MESNA (100 µM) or MESNA (100 µM) alone for 24 hr and were subjected to LDH assay and compared to control (vehicle only) cells. These results are shown in FIG. 4A. The inclusion of 100 MESNA with PbTx-2 (5 µM) reduced the PbTx-2 cytotoxicity by approximately 50% (from 48% to 26% relative to control). The difference in cytotoxicity between the PbTx-2 treated and the PbTx-2 & MESNA treated samples was statistically significant (p<0.001, n=6).

Comparative analysis of the redox status of protein cysteine residues in human lymphoblast cells was performed after 24 h exposure to the principal Florida red tide toxin PbTx-2 (5 µM) in parallel with co-administration of 5 µM of PbTx-2 and 500 µM of MESNA, relative to untreated (control) cells. Redox proteomics utilizes cysteine reactive tags to study reversible cysteine modifications.

Figure 5:
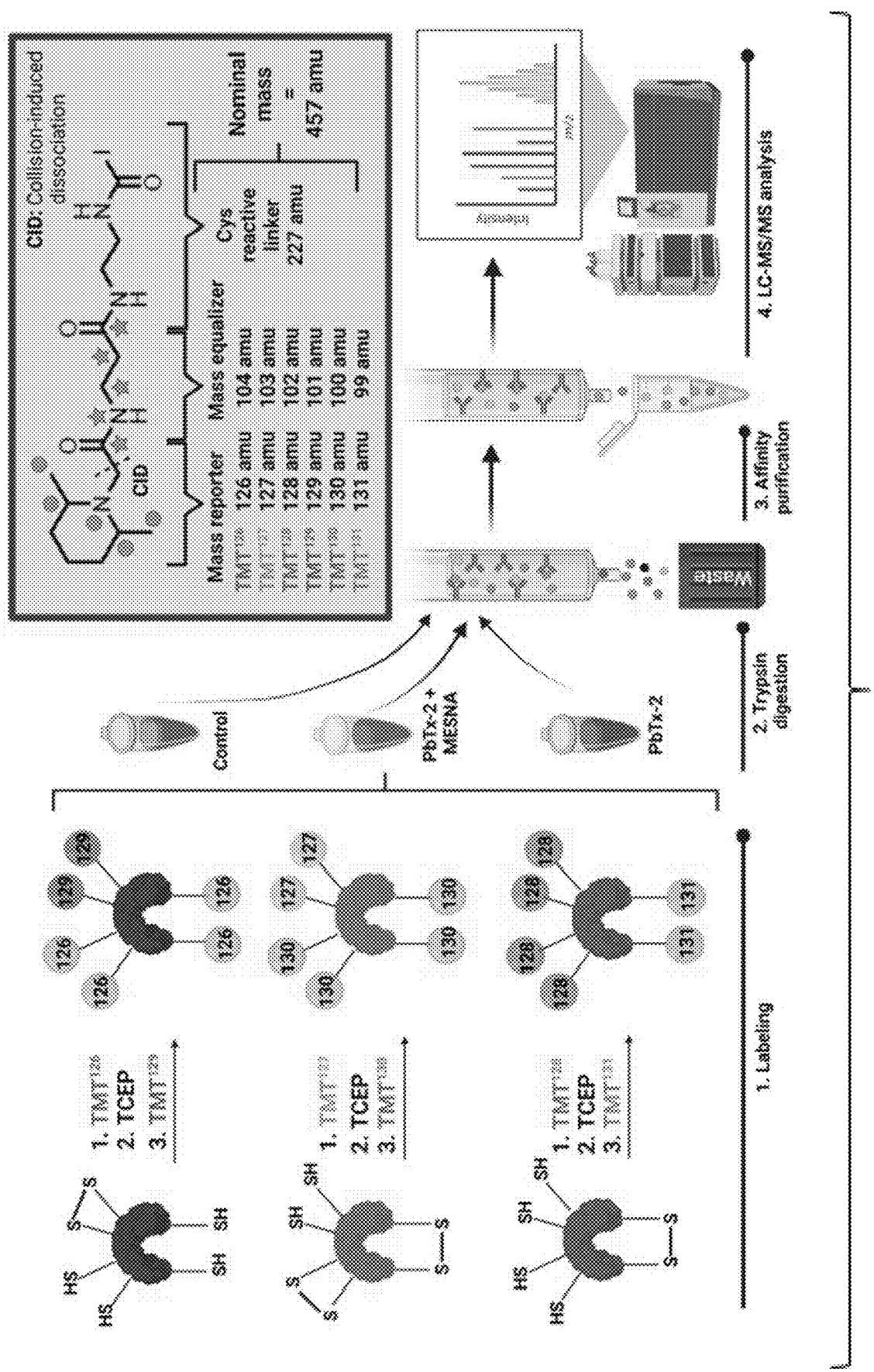

The redox proteomics workflow, utilizing isobaric tandem mass tags (TMT) for peptide labeling is outlined in FIG. 5. The isotopically labeled reporters are balanced by the mass equalizer, such that all TMT reagents have the same nominal mass. Reduced thiols are alkylated using a the light TMT reagent, after which the proteins are be exposed to tris(2-carboxyethyl)phosphine (TCEP), a reducing agent which reduces disulfides, sulfenic acids (—SOH) and S-nitrosothiols (—SNO) to free thiols. These newly reduced thiol groups are then alkylated by a heavy TMT, and the isolated proteins are trypsinized and labeled peptides are enriched before analysis. Peptide sequences along with reporter ion intensities are obtained by tandem mass spectrometry (MS/MS). The approach allows for higher sensitivity, and less complexity in the data when compared to a solely MS-based technique as isotopically labeled peptides co-elute, while the differential reporters are resolved by MS. The relative intensities of the reporters vary according to the original redox state of the cysteines.

In total, 2617 proteins were identified with high confidence by tandem MS from 5 replicates of each treatment group: (i) control (ii) PbTx-2 (5 µM) and (iii) PbTx-2 (5 µM) & MESNA (500 µM). The average redox state for all 2617 proteins for each treatment is shown in Table 1 along with the p values of a two-tailed paired t-test comparing the PbTx-2 treated samples to the control, the PbTx-2 & MESNA samples to the control and the PbTx-2 & MESNA treated samples to the PbTx-2 treated samples. Referring to equation (1) a smaller redox state means that the cysteines in the sample are more oxidized. Among the three treatment groups, the PbTx-2 treatments showed the lowest average redox state of 59% compared to 71% for the control treatments.

TABLE 1

Average redox state for all 2617 proteins and ρ values from a two-tailed paired t-test comparing treatments.

| Treatment | Average redox state | Median redox state |
|---|---|---|
| Control | 0.71 | 0.74 |
| PbTx-2 (5 µM) | 0.59 | 0.62 |
| PbTx-2 (5 µM) and MESNA (500 µM) | 0.77 | 0.82 |
| Two-tailed paired t-test | | |
| PbTx-2/Control | p = 4.7 E-90 | |
| PbTx-2 & MESNA/Control | p = 1.1 E-31 | |
| PbTx-2 & MESNA/PbTx-2 | p = 0 | |

Figure 6A:
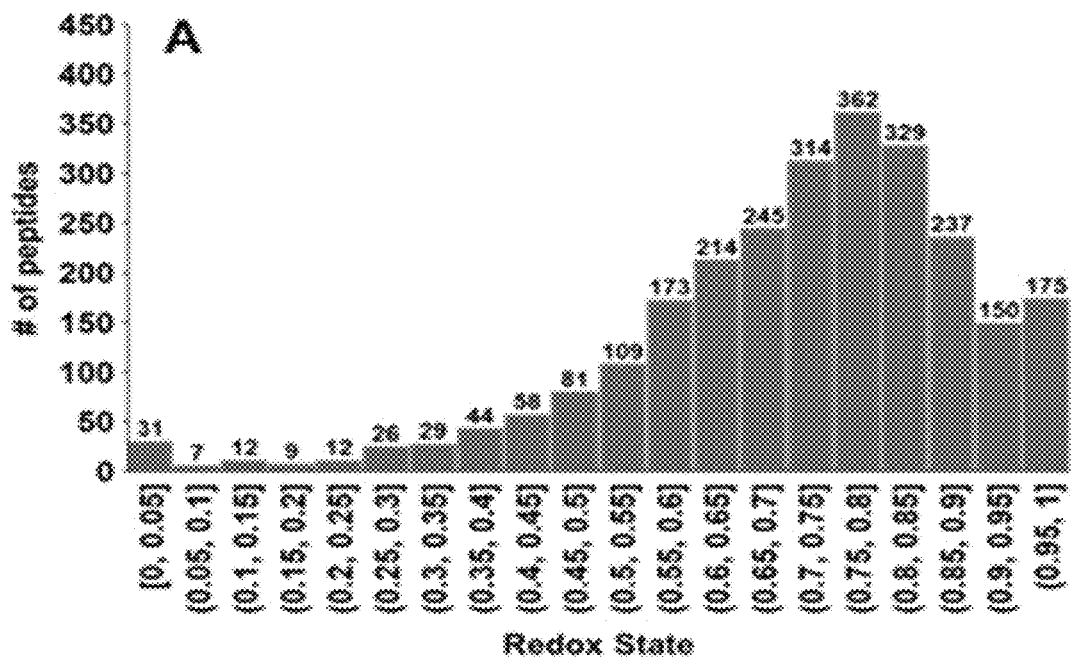
Figure 6B:
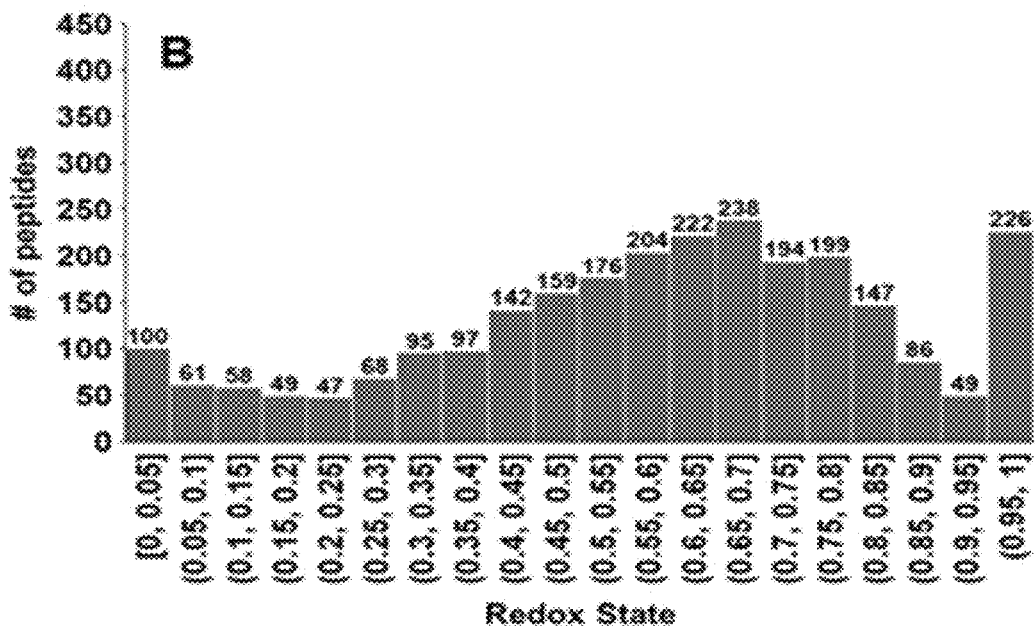
Figure 6C:
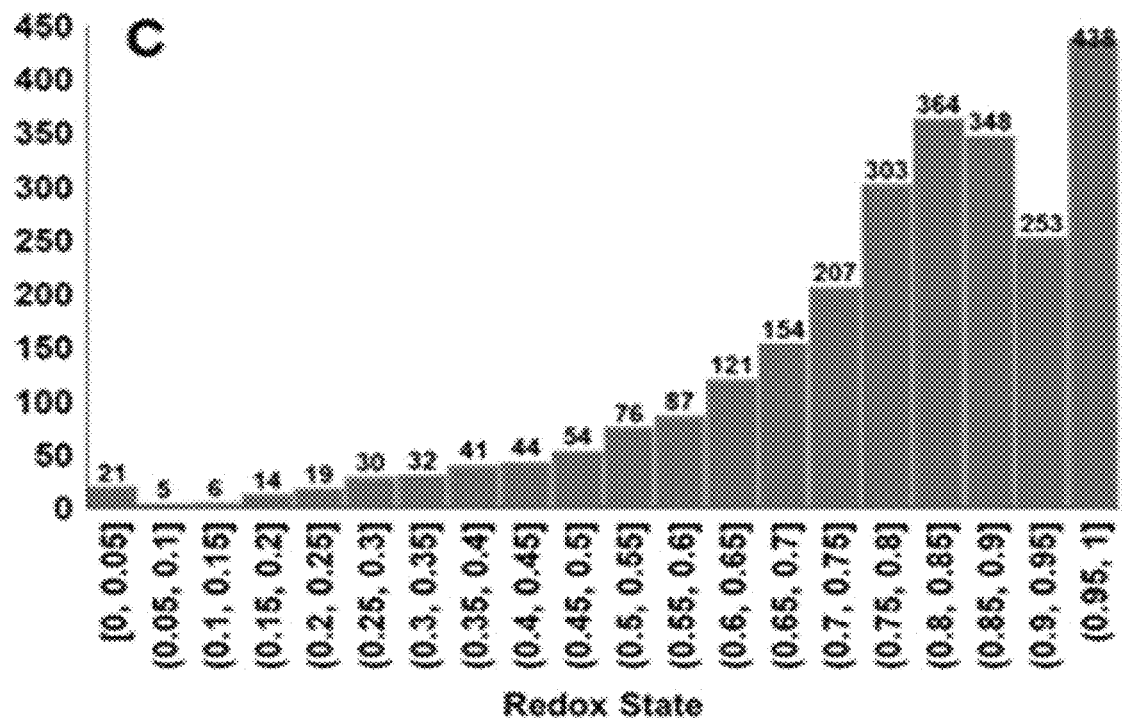

These data are illustrated graphically in FIGS. 6A-6C, which are histograms of the redox states for the control, PbTx-2 and PbTx-2 & MESNA treated samples for all 2617 proteins across the five data sets. The result shows that treatment of lymphoblast cells with 5 µM PbTx-2 for 24 hours causes a significant oxidation of the redoxome. Also, the addition of 500 µM MESNA with the 5µM PbTx-2 shifts the redox state towards and even beyond the control levels (average redox state of the 5 replicates: 77%).

Figure 6D:
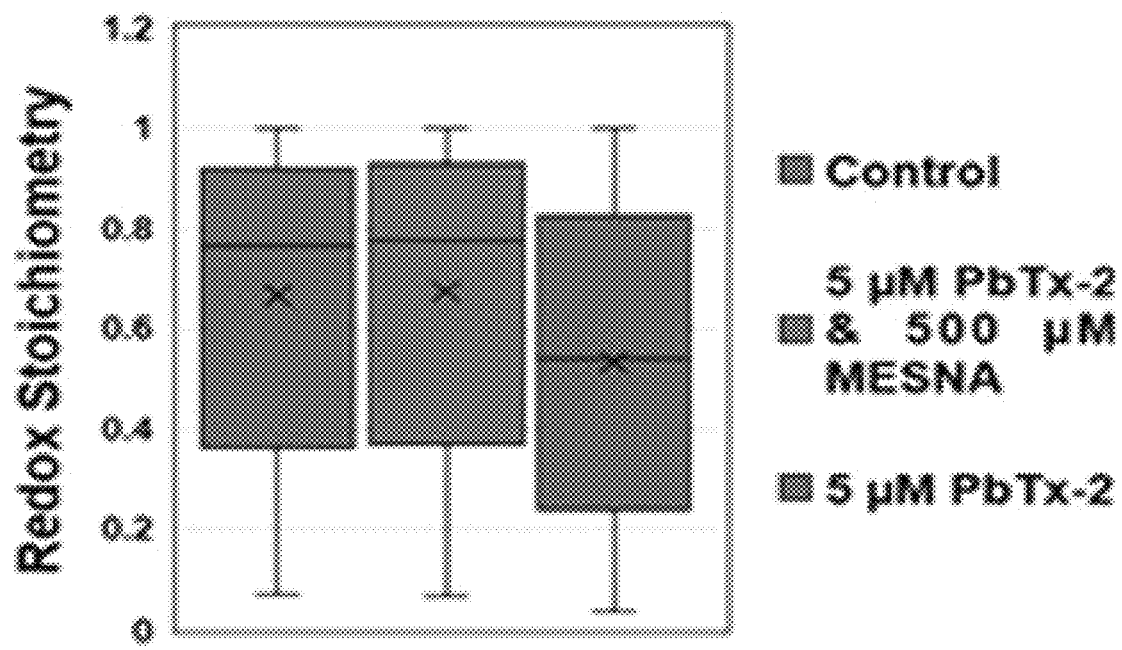

Naturally, between the three treatments, individual proteins would be oxidized or reduced to different degrees. Nonetheless, these results display the effects on the global redoxome. Among the 2617 proteins identified across the five replicate treatments, 606 (24%) appeared in three or more data sets allowing for robust statistical comparisons of treatment conditions. The result shows that the 5 μM PbTx-2 treated samples display lower redox states and the combination treatment with 500 μM MESNA and 5 μM PbTx-2 restores the redox states to control levels or slightly higher (FIG. 6D).

The effects of PbTx-2 and the PbTx-2 & MESNA on the redox state of the 606 individual proteins that appeared in three or more replicates, in comparison to the control, are graphically represented as volcano plots (FIG. 7). A volcano plot is a plot of the $\log_2$ of the fold change in an observation between two conditions on the x-axis vs. the $\log_{10}$ of the corresponding p-value from a student's t-test, for each observation. Fold changes ~1 will appear near zero on the x-axis of a volcano plot and each increment of 1 represents a two-fold change. Thus, a $\log_{10}$(fold change) of <1 would represent a change in the negative direction (in this case a more oxidized protein) and a logio(fold change) of >1 would represent a change in the positive direction (in this case a more reduced protein).

Figure 7A:
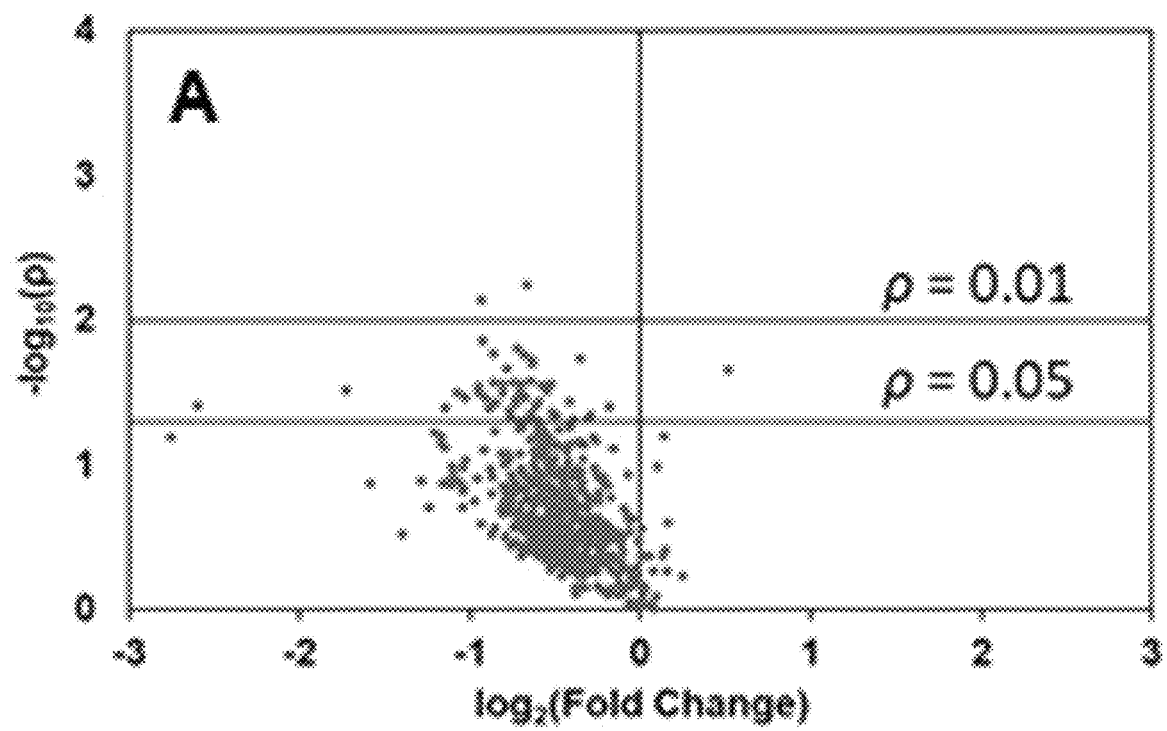
Figure 7B:
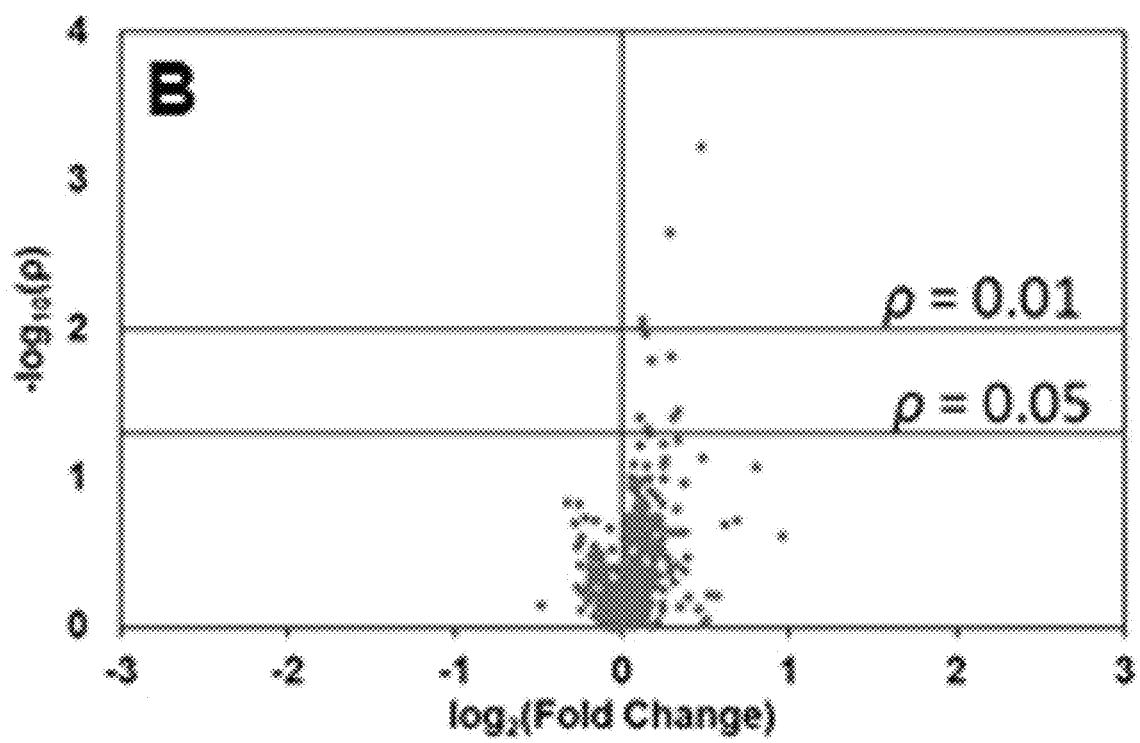

As shown in FIG. 7, by the shift of the individual points towards the negative direction along the x-axis, most of the peptides are more oxidized in the PbTx-2 treated cells (FIG. 7A). In total, 54 of the 606 proteins had a significantly different redox state at the 95% confidence level (−log p≥1.3), and of those 54, 2 of them were significant at the 99% confidence level (−log p≥2). Of those 54 proteins with significant differences in redox state, only one protein (Plexin-B2, fold change=1.41, −$\log_{10}$p=1.68) was more reduced, and the other 53 were significantly more oxidized. The counteracting effect of MESNA is demonstrated by comparing the combination treatment of the PbTx-2 & MESNA to the control (FIG. 7B), with the volcano plot returning to a more expected symmetrical distribution with a clustering of the $\log_{10}$ of redox states around zero. In total, only 12 proteins of the 606 had a significantly different redox state at 95% confidence, and of those 12, 4 of them were significant at a 99% confidence level, and all the proteins that were significantly different redox state were more reduced when compared to the control.

Figure 8A:
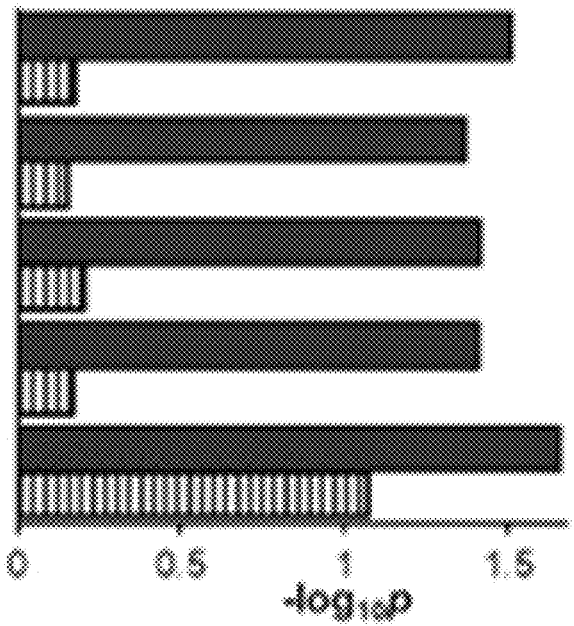
Figure 8B:
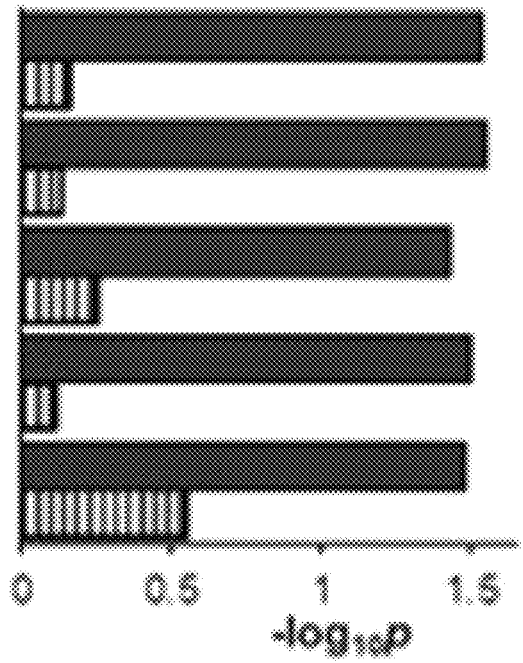
Figure 8C:
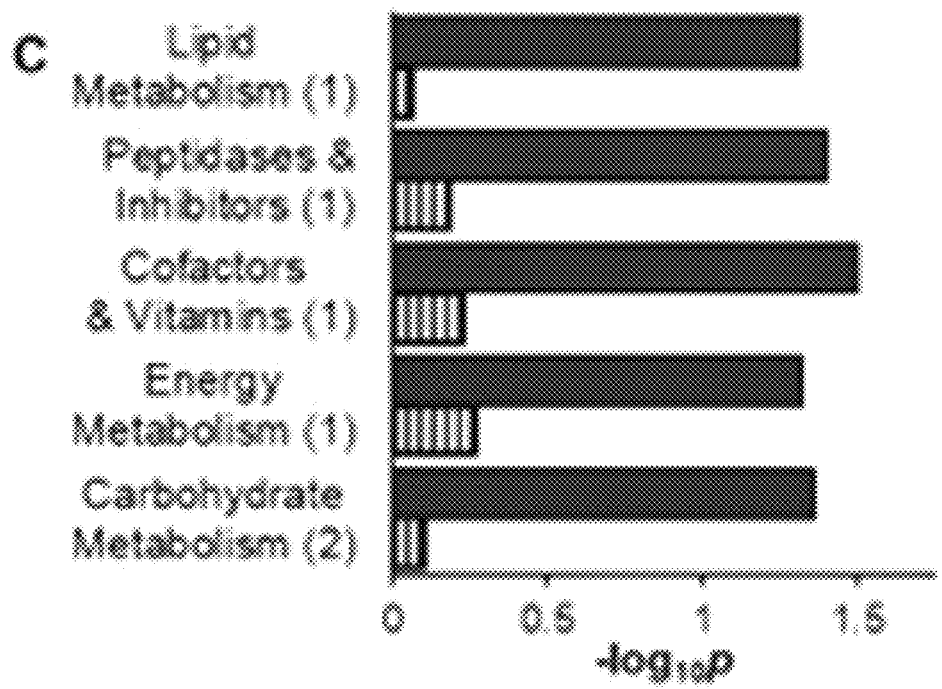

The 54 proteins with significantly different redox status were classified according to their KEGG identifiers as related to genetic information processing (33), metabolism (6), cellular transport and catabolism (3), signaling and cellular processes (2) and organismal systems (1). Nine proteins could not be classified. These data are shown in FIG. 8A. The two most highly represented classes (genetic information processing and metabolism) are further subdivided in FIGS. 8B and 8C. The redox status of all 54 proteins with significantly altered redox state as a result of PbTx-2 treatment, were restored to control levels when treated simultaneously with MESNA. Notably, thioredoxin (Trx) was found among the 54 proteins with significantly altered redox state with only 29% of cysteines reduced compared to 51% for the control. The redox state of Trx was restored to 47% in the PbTx-2 & MESNA treated cells. On the other hand, no pathways were overrepresented among the 12 proteins with significantly altered redox status in the PbTx-2 & MESNA treatment.

The inhibition of TrxR-1 by the dinoflagellate toxin PbTx-2 causes a shift in the redox status of the proteome. The results further demonstrated that MESNA could reduce the cytotoxicity of PbTx-2. The most significant finding from the redox proteomics analysis is the massive shift in the global redox state of the proteome of PbTx-2 treated cells. Among the significantly oxidized proteins, more than half were related to genetic information processing. This includes Trx (fold change=0.67, p=0.026) the principal target of TrxR, and the chaperone DnaJA2 (fold change=0.75, p=0.045). Both are classified under protein folding, sorting and degradation. The fold change for Trx in the PbTx-2 & MESNA treated cells is 1.03 or virtually unchanged. Since the thioredoxin system is a major regulator of redox homeostasis, this change alone could have significant implications for the global redoxome.

EXAMPLE 3-CHANGES IN EXPRESSION

Figure 9A:
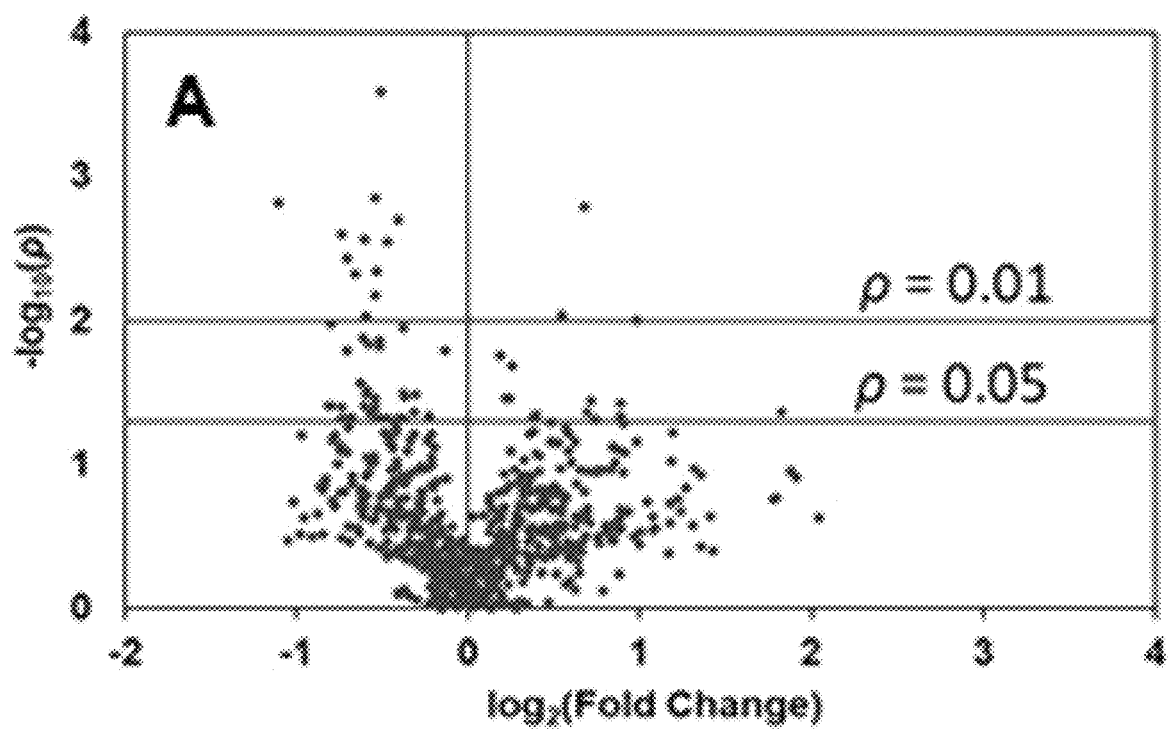
Figure 9B:
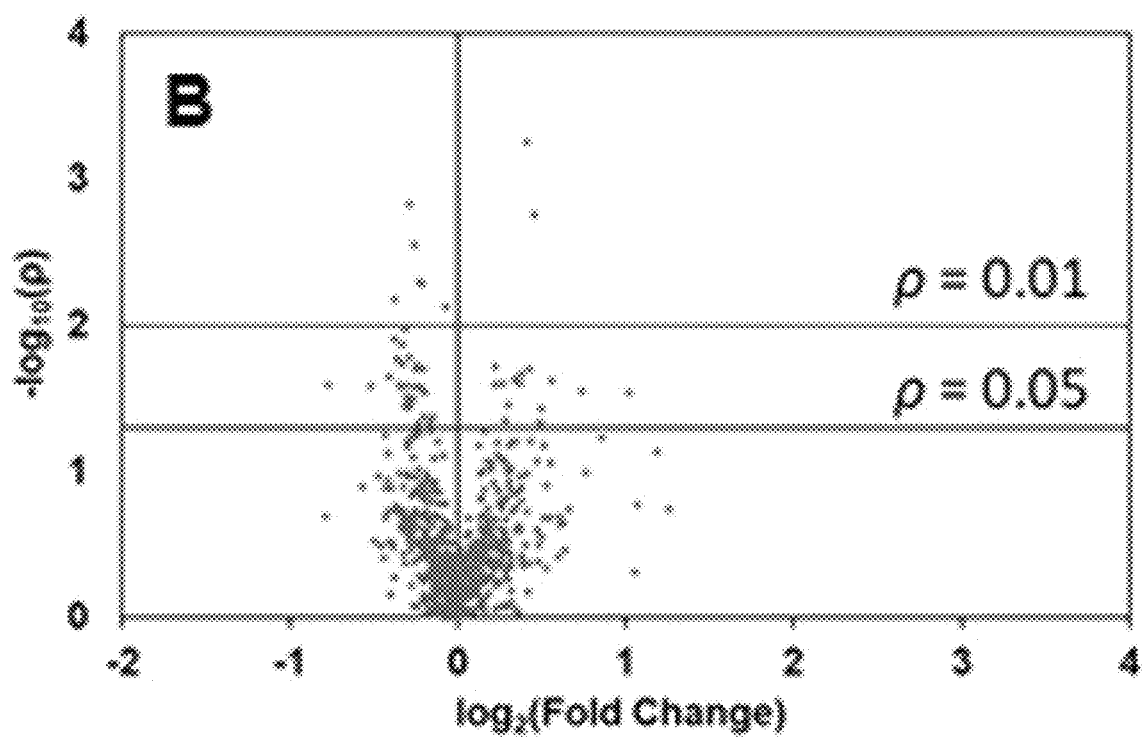
Figure 10:
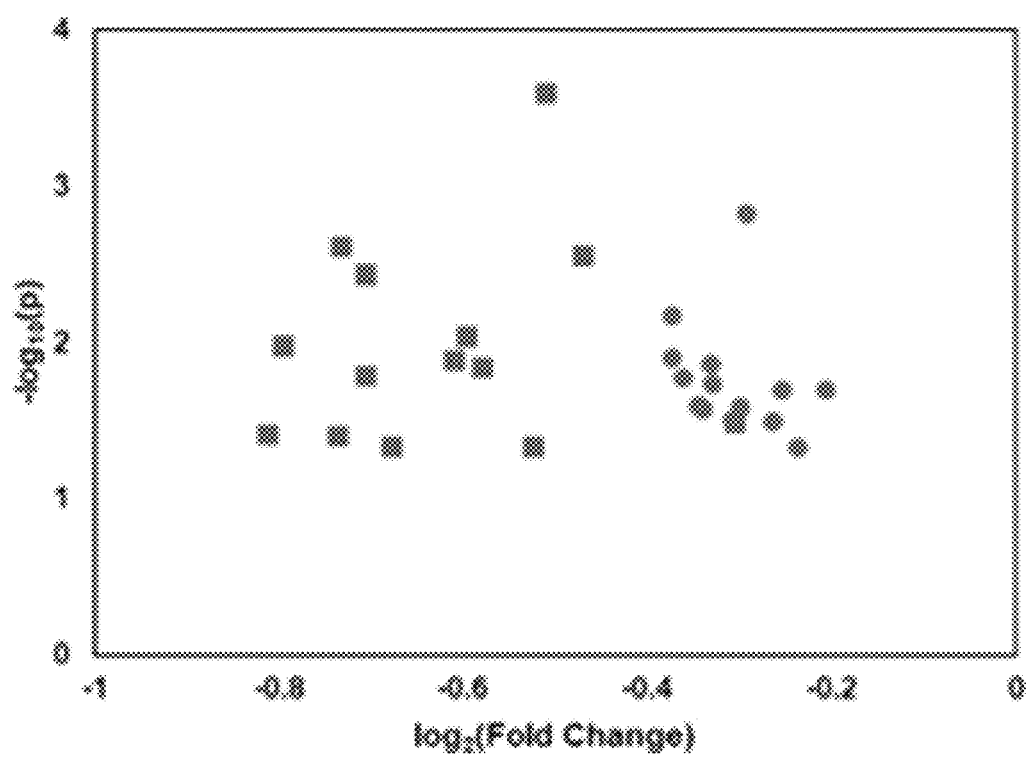

Cysteine reactive TMTs are infrequently used to study changes in protein expression. Given the relatively low natural occurrence of cysteine residues in proteins, cysteine containing peptides represent relatively small fraction of the total peptide content. Expression data can be extracted from cysteine reactive TMT labeling. Volcano plots of the fold change of expression of individual proteins for the PbTx-2 vs control, PbTx-2 & MESNA vs control and PbTx-2 & MESNA vs. PbTx-2 are shown in FIG. 9. In total, 56 proteins of the 606 that appeared three or more times had significantly different expression at the 95% confidence level in the PbTx-2 treated samples when compared with the control (FIG. 9A) and of those 56, 15 of them were significant at the 99% confidence level. Fifty proteins of the 606 proteins had a significantly different expression at the 95% confidence level in the PbTx-2 & MESNA treated samples when compared with the control (FIG. 9B) and of those 50, 36 of them were significant at the 99% confidence level. There were 14 proteins with significant changes in expression in both the PbTx-2 and the PbTx-2 & MESNA treated samples when compared to the control. In other words, the expression of these 14 proteins was not restored to control levels with the inclusion of MESNA in the treatment. In every instance the fold change was <1 for the PbTx-2 treated cells and closer to 1 for the PbTx-2 & MESNA treated cells (FIG. 10).

Figure 11A:
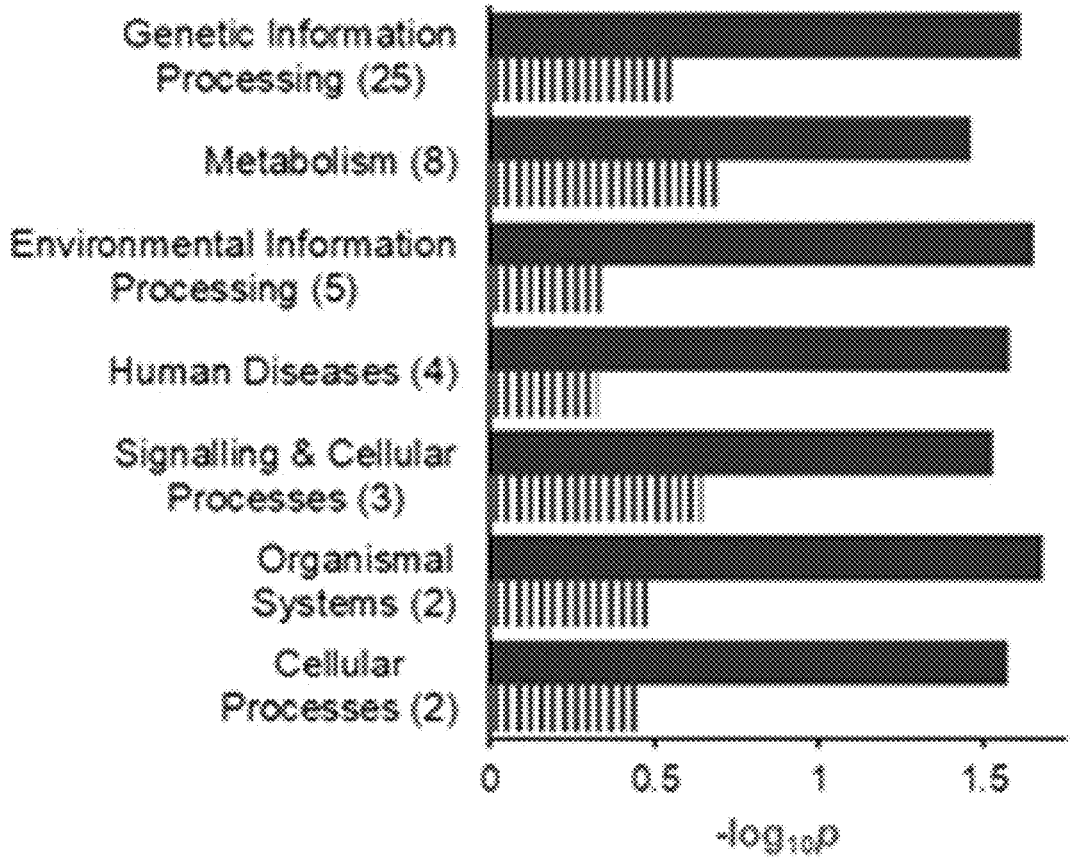
Figure 11B:
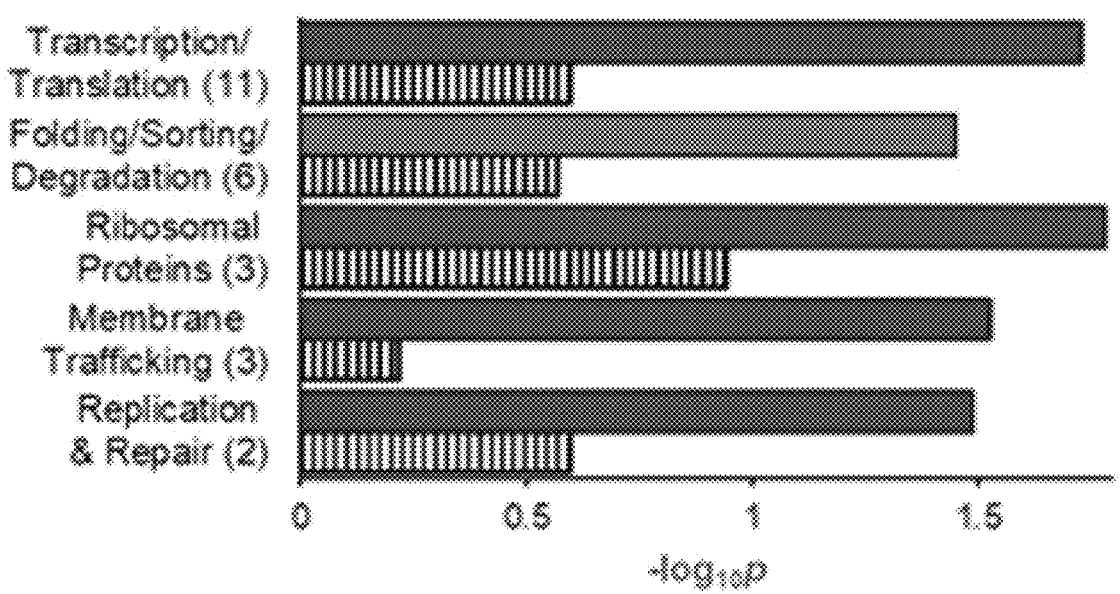
Figure 11C:
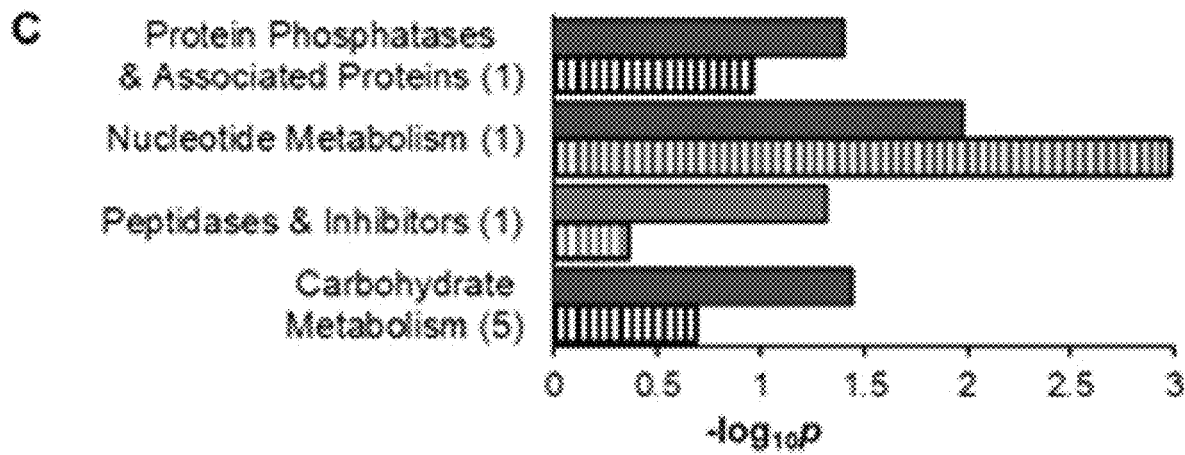

According to the KEGG classifications, the 56 proteins with significantly different expression were classified as related to genetic information processing (25), metabolism (8), environmental information processing (5), human diseases (4), signaling and cellular processes (3) cellular processes (2) and organismal systems (2). Seven proteins could not be classified (FIG. 11A). The two most highly represented classes (genetic information processing and metabolism) are further subdivided in FIGS. 11A and 11B. The redox status of all 54 proteins with significantly altered redox status as a result of PbTx-2 treatment, were restored to control levels when treated simultaneously with MESNA.

EXAMPLE 4—PROTEIN LOCALIZATION

Figure 12A:
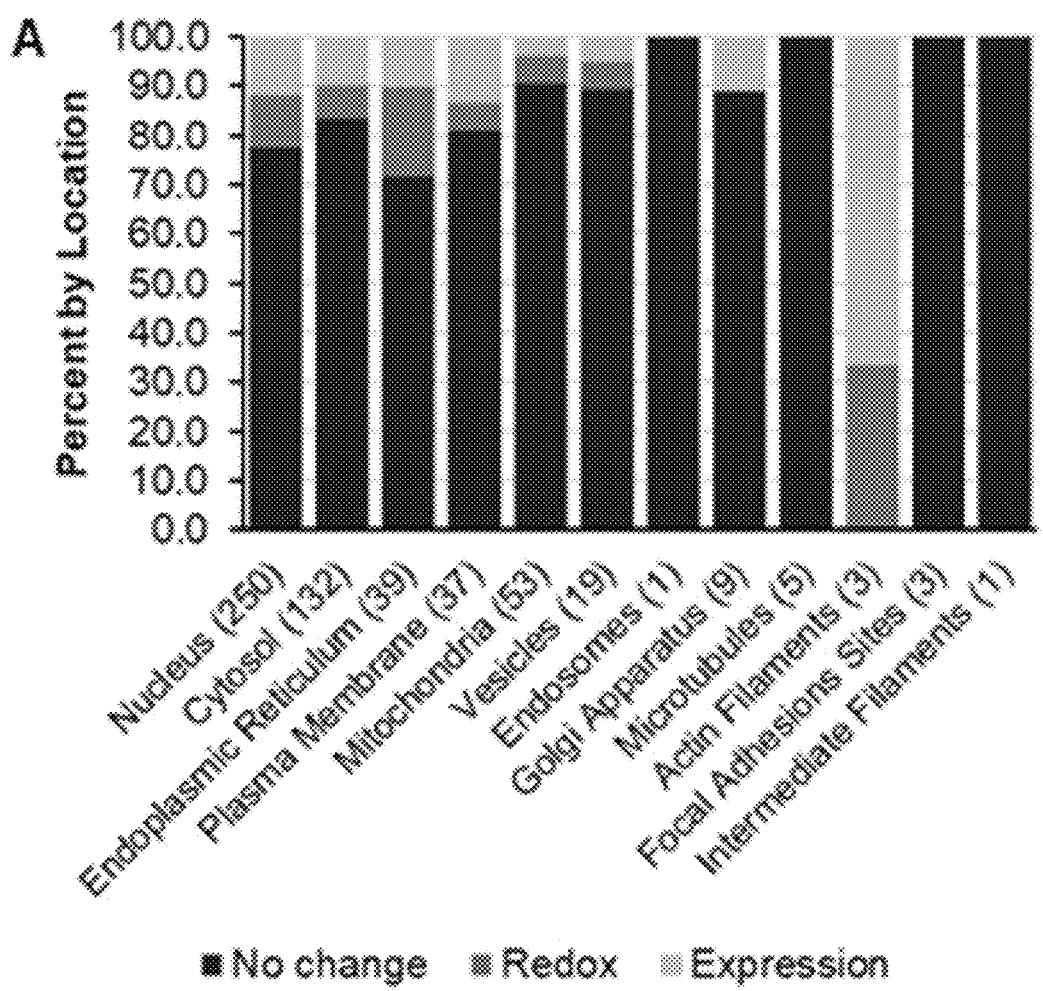
Figure 12B:
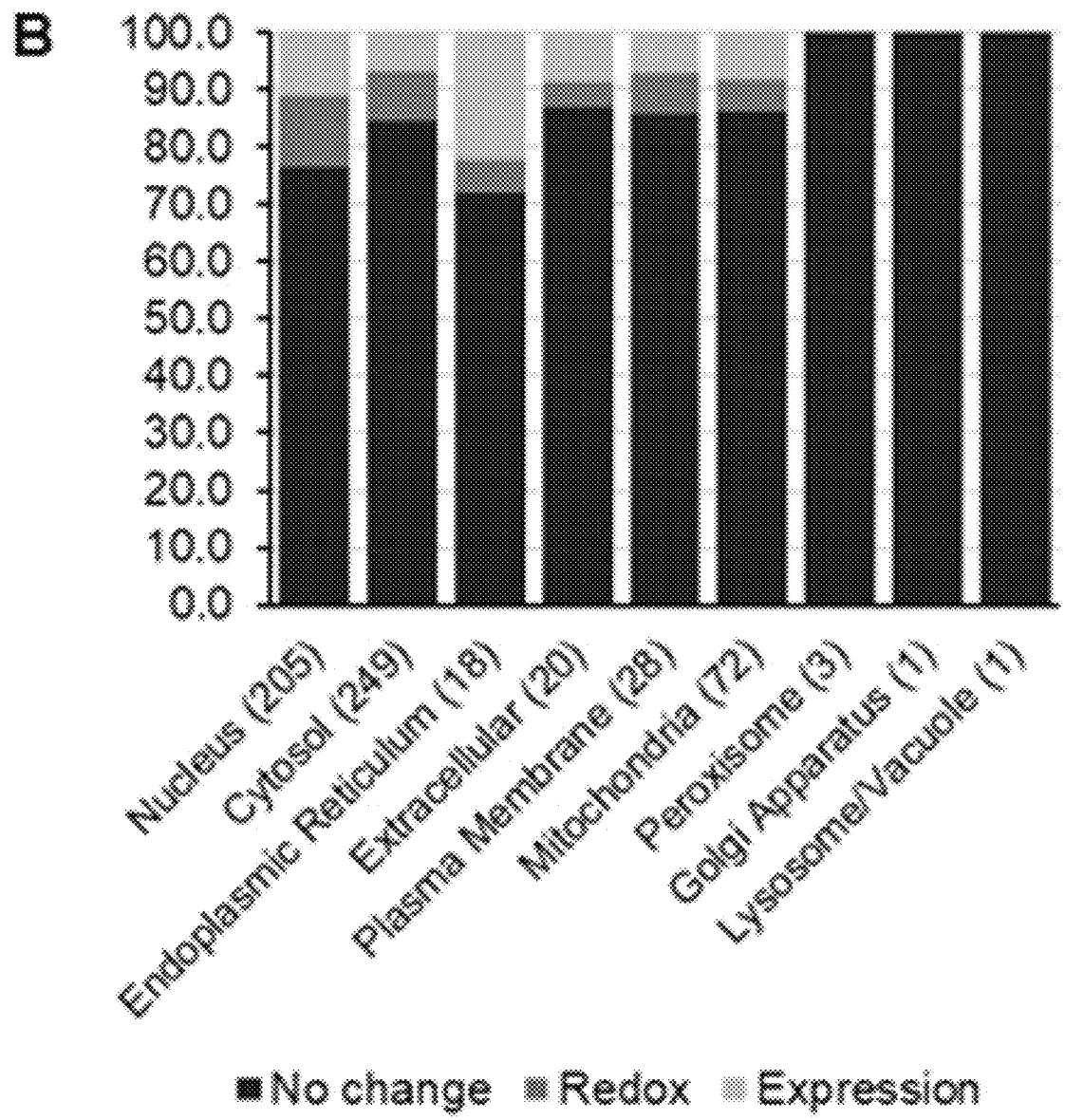

Two approaches were taken for subcellular localization of the 606 proteins that occurred in three or more replicates. Gene codes were entered into the Human Protein Atlas (www.proteinatlas.org). This database derives from immunofluorescence microscopy data and maps 12,003 human proteins into 30 subcellular compartments. In addition, full length sequences were submitted to DeepLoc 2.0, which sorts proteins into 10 subcellular compartments based on sequence profiles. Using the Human Protein Atlas 525 of the 606 proteins could be localized 552 times (some proteins localized to two or more compartments). Using Deeploc 2.0, 600 proteins were each localized to a single compartment. As shown in FIG. 12, both approaches provided similar results.

Apart from proteins that localized to actin filaments (which were only three), the subcellular compartments with highest fraction of significantly altered proteins were the endoplasmic reticulum followed by the nucleus. All proteins which localized to the ER and that were significantly altered in redox state (7) or expression (4) were associated with genetic information processing. Twenty of 29 proteins in the nucleus that exhibited significant changes in expression were related to genetic information processing. Ten of 23 proteins in the nucleus that exhibited significant changes in redox state were related to genetic information processing. Four out of 9 proteins that were significantly altered in redox state in the cytosol were related to genetic information processing. Seven out of ten proteins that were significantly altered in expression in the cytosol were related to genetic information processing. Two proteins in the cytosol exhibited significant changes in redox state and both were related to genetic information processing.

In the subject invention, the PbTx-2-induced oxidative stress was evaluated in human lymphoblasts by redox proteomics. The inhibition of TrxR-1 by the dinoflagellate toxin PbTx-2 causes a shift in the redox state of the proteome to a more oxidized state. MESNA could lessen the PbTx-2 cytotoxicity by mitigating oxidative stress either by PbTx-2 scavenging or through its antioxidant activity. The most significant finding from the redox proteomics analysis is the massive shift in the global redox state of the proteome of PbTx-2 treated cells. The cytosolic thioredoxin Trx-1, the principal target of TrxR-1, and the ubiquitous antioxidant enzymes peroxyredoxins (Prxs) are among the most notable overoxidized proteins. The fold change in redox state and the p values for these enzymes are shown in Table 2.

Trx-1 was identified in all five replicates. More importantly, the active site cysteine residues of Trx-1 were identified in four of five replicates. The fold change for the PbTx-2 treated samples for these specific cysteine residues, relative to the control was 0.62 (p=0.043). Since the thioredoxin system is a major regulator of redox homeostasis, the oxidation of these active site cysteines of Trx-1 alone could have significant implications for the global redoxome. The mitochondrial Trx-2 was identified in four of five replicates. It is noteworthy that, neither the redox states of all cysteines nor the active site cysteines of Trx-2 were significantly different from the control for either the PbTx-2 treated cells, or the cells co-treated with PbTx-2 and MESNA.

TABLE 2

Fold change in redox state compared to control for Trxs and Prxs for all cysteines and active-site cysteines and p values from a two-tailed paired t-test comparing treatments (p ≤ 0.05 are shown in bold)

| Enzyme | PbTx-2 | | PbTx-2 & MESNA | |
|---|---|---|---|---|
| | Fold change | p value | Fold change | p value |
| Trx-1 all cysteines | 0.67 | 0.026 | 1.03 | 0.77 |
| Trx-1 active site cysteines | 0.62 | 0.043 | 0.97 | 0.80 |
| Trx-2 all cysteines | 0.72 | 0.23 | 0.98 | 0.88 |
| Trx-2 active site cysteines | 0.92 | 0.25 | 1.1 | 0.91 |
| Prx all cysteines | 0.70 | 0.21 | 0.99 | 0.75 |
| Prx all peroxidatic cysteines ($C_P$) | 0.61 | 0.10 | 1.02 | 0.74 |
| peroxidatic w/o Prx-3 | 0.57 | 0.018 | 1.00 | 0.91 |
| Prx all resolving cysteines ($C_R$) | 0.60 | 0.016 | 1.01 | 0.84 |
| resolving w/o Prx-3 | 0.59 | 0.015 | 1.00 | 0.97 |

The instant dataset included peptides from peroxyredoxins (Prxs) 1, 3, 5 and 6 across all 5 datasets. Prxs catalyze the reduction of $H_2O_2$ and organic hydroperoxides to water and alcohols respectively. Prxs have one highly conserved and one semi-conserved cysteine residue. The highly conserved cysteine, known as the peroxidatic cysteine ($C_P$), is found in the N-terminal sequence motif PXXXTXXC (SEQ ID NO: 1).

During the catalytic cycle, this cysteine residue, reduces peroxides with concomitant oxidation to the sulfenic acid (R-SOH). The semi-conserved C-terminal cysteine of 2-Cys Prxs, known as the resolving cysteine ($C_R$), attacks the R-SOH, to release water or alcohol, forming a disulfide bridge. 1-Cys Prxs do not have a CR and this step is performed by a low molecular weight thiol or another protein. The resulting disulfide bridge may be reduced by Trx, glutaredoxin (Grx), or another dithiol.

Interestingly, the oxidized form of Prx may function as a molecular chaperone, facilitating the proper folding of proteins through the redox-dependent isomerization of disulfide bonds. Examination of all cysteine residues in Prxs shows no significant differences in PbTx-2 treated cells (Table 2). When $C_P$ (10 occurrences across 5 data sets) and $C_R$ (10 occurrences across 3 data sets) were analyzed separately, significant differences for $C_R$ (fold change=0.60, p=0.016) but not for $C_P$ (fold change=0.61, p=0.10) were observed.

The only $C_P$ that was more reduced in the PbTx-2 treated cells was from Prx-3, which is localized exclusively to the mitochondria. As Prxs are reduced by Trx and the redox state of the mitochondrial Trx-2 was not affected by PbTx-2 treatment, the single occurrence of $C_P$ of Prx-3 was removed from the analysis. The results show that the redox state of the Cps without Prx-3 is significantly different from the control (fold change=0.57, p=0.018). Cells co-treated with PbTx-2 and MESNA did not differ significantly from the control.

Among the significantly oxidized proteins, more than half were related to genetic information processing. This group includes the eIF2β subunit (fold change=0.63, p=0.015). The α-subunit of eIF2 is a key factor in the unfolded protein response (UPR) cascade. The UPR is initiated under various types of endoplasmic reticulum (ER) stress, including conditions of oxidative stress, to manage the load of oxidized, misfolded, or unfolded proteins.

During the UPR numerous ER-resident protein folding chaperones are upregulated. Concurrently, protein synthesis is downregulated by phosphorylation of eIF2α by PERK (PKR-like endoplasmic reticulum kinase) to relieve the accumulation of unfolded or misfolded proteins. eIF2β was found to have the $H_2O_2$-sensitive $Zn^{2+}$-finger motif ($CX_2C$-$X_{19}$-$CX_2C$; SEQ ID NO: 2.). This motif was identified in eIF2β in four of the five replicates. These cysteines were significantly more oxidized in the PbTx-2 treated samples (fold change=0.19, p=0.042) and were restored to control levels (fold change=0.93, p=0.061) in the PbTx-2 and MESNA treated samples.

The KEGG classification having the largest number of significant changes in expression was also genetic information processing. Noteworthy is the fact that all subcategories were downregulated apart from protein folding/sorting and degradation. The four top upregulated proteins in PbTx-2 treated cells were protein folding chaperones, each localized to the ER. The fold change and p value for a student's t-test for these four proteins are shown in Table 3.

TABLE 3

Fold change and p values for chaperones which were overexpressed in the PbTx-2 treated cells.

| Chaperone | PbTx-2 Fold Change | p = | PbTx-2 & MESNA Fold Change | p = |
|---|---|---|---|---|
| Protein disulfide isomerase A4 (PDIA4) | 3.55 | 0.043 | 1.22 | 0.10 |
| Protein disulfide isomerase A3 (PDIA3) | 1.85 | 0.0046 | 1.30 | 0.37 |
| Selenoprotein F (SELENOF) | 1.85 | 0.037 | 1.11 | 0.32 |
| T-complex protein 1 (TCP-1) | 1.60 | 0.001 | 1.20 | 0.44 |

The top two upregulated proteins were protein disulfide isomerases A4 and A3 (PDIA4 and PDIA3). These redox regulated chaperones carry two thioredoxin-like CGHG motifs, which function to isomerize non-native disulfide bonds of target proteins by thiol-disulfide exchange to promote proper folding and prevent misfolding or aggregation. The tailless complex polypeptide 1 (TCP-1) or chaperonin TCP-1 (CCT) is an oligomeric complex that is responsible for folding its obligate substrates actin and tubulin and several other lower abundance proteins. Six subunits of CCT were present in the dataset with fold change relative to control ranging from 2.11 to 1.28. However, only the change in the alpha subunit was statistically significant.

Seleno protein F (SELENOF) is a redox-sensitive Sec containing protein having a CXU motif in its N-terminal, (Trx)-like domain. Though less well studied than other chaperones, structural studies suggest that SELENOF may exhibit thiol—disulfide oxidoreductase activity and may also play a role in the folding of glycoproteins. This selenoprotein is upregulated under conditions of endoplasmic reticulum stress and the unfolded protein response.

Nine of the 11 proteins with significantly altered expression, that fell under the KEGG classification of transcription and translation, were downregulated. This downregulated group included, four ribosomal proteins, DNA-directed RNA polymerase II, transcription, translation, and RNA splicing factors. Cytosolic translation is regulated under various stress conditions including ER stress and the UPR.

All publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method for treating brevetoxin poisoning in a subject, the method comprising administering to the subject who has been poisoned by, exposed to, or at risk for exposure to, brevetoxin a composition comprising sodium mercaptoethyl sulfonate (MESNA), wherein the brevetoxin is PbTx-2.

2. The method of claim 1, the composition further comprising ascorbic acid.

3. The method of claim 1, the composition being administered through oral, nasal, topical, transdermal, intramuscular, intravenous administration.

4. The method of claim 1, the composition being administered through inhalation.

5. A method for inhibiting or suppressing oxidative stress induced by a brevetoxin in a subject, the method comprising administering to the subject who has been poisoned by, exposed to, or at risk for exposure to, the brevetoxin a composition comprising sodium mercaptoethyl sulfonate (MESNA), wherein the brevetoxin is PbTx-2.

6. A method for treating neurotoxic shellfish poisoning, the method comprising administering to a subject who has consumed brevetoxin tainted shellfish a composition comprising sodium mercaptoethyl sulfonate (MESNA), wherein the brevetoxin is PbTx-2.

7. A method for inhibiting or suppressing oxidative stress induced by a brevetoxin in a cell, the method comprising contacting the cell that has been exposed to the brevetoxin a composition comprising sodium mercaptoethyl sulfonate (MESNA), wherein the brevetoxin is PbTx-2.

8. The method of claim 5, the composition further comprising ascorbic acid.

9. The method of claim 5, the composition being administered through oral, nasal, topical, transdermal, intramuscular, intravenous administration.

10. The method of claim 5, the composition being administered through inhalation.

11. The method of claim 6, the composition further comprising ascorbic acid.

12. The method of claim 6, the composition being administered through oral, nasal, topical, transdermal, intramuscular, intravenous administration.

13. The method of claim 6, the composition being administered through inhalation.

* * * * *